US012589053B2

(12) United States Patent
Yuki et al.

(10) Patent No.: US 12,589,053 B2
(45) Date of Patent: Mar. 31, 2026

(54) SYSTEM FOR DETECTING POSITION OF DISTAL END OF MEDICAL TUBE

(71) Applicants: JMS Co., Ltd., Hiroshima (JP); MDI CO., LTD., Yaizu (JP); KURUME UNIVERSITY, Kurume (JP)

(72) Inventors: Takehiko Yuki, Hiroshima (JP); Koichiro Toyota, Hiroshima (JP); Manabu Mochizuki, Shizuoka (JP); Yasuo Imamura, Shizuoka (JP); Masahiro Kinoshita, Fukuoka (JP); Osuke Iwata, Fukuoka (JP)

(73) Assignees: JSM Co., Ltd., Hiroshima (JP); MDI Co., Ltd., Shizuoka (JP); Kurume University, Fukuoka (JP)

( * ) Notice: Subject to any disclaimer, the term of this patent is extended or adjusted under 35 U.S.C. 154(b) by 697 days.

(21) Appl. No.: 17/632,353

(22) PCT Filed: Aug. 3, 2020

(86) PCT No.: PCT/JP2020/029697
§ 371 (c)(1),
(2) Date: Feb. 2, 2022

(87) PCT Pub. No.: WO2021/024992
PCT Pub. Date: Feb. 11, 2021

(65) Prior Publication Data
US 2022/0287917 A1 Sep. 15, 2022

(30) Foreign Application Priority Data

Aug. 5, 2019 (JP) ................................. 2019-143894

(51) Int. Cl.
*A61J 15/00* (2006.01)
*A61M 39/10* (2006.01)

(52) U.S. Cl.
CPC ....... *A61J 15/0088* (2015.05); *A61J 15/0011* (2013.01); *A61M 39/10* (2013.01); *A61M 2039/1033* (2013.01)

(58) Field of Classification Search
None
See application file for complete search history.

(56) References Cited

U.S. PATENT DOCUMENTS 3,866,599 A 2/1975 Johnson
4,567,882 A 2/1986 Heller
(Continued)

FOREIGN PATENT DOCUMENTS

DE 36 03 782 10/1987
EP 0 131 659 1/1985
(Continued)

OTHER PUBLICATIONS

International Search Report issued in International Application No. PCT/JP2020/029697, Sep. 1, 2020, 7 pages w/translation.
(Continued)

*Primary Examiner* — Amanda L Steinberg
*Assistant Examiner* — James Moss
(74) *Attorney, Agent, or Firm* — HSML P.C.

(57) ABSTRACT

A tube distal end position detection system (1) includes a light source device (50) that emits light, a hollow tube (10) having a flow path (11) that allows a liquid to flow through, a connector (20) provided at a base end of the tube so as to allow light from the light source device to be incident on an end surface (12) at the base end of the tube, and a light emitting portion (30) provided at the distal end of the tube. Light from the light source device passes through the tube and is emitted from the light emitting portion and transmitted to the body surface.

19 Claims, 15 Drawing Sheets

(56) References Cited

U.S. PATENT DOCUMENTS

| 10,631,930 | B1 | 4/2020 | Miyagawa et al. |
| 2004/0197061 | A1 | 10/2004 | Ogura et al. |
| 2006/0036164 | A1 | 2/2006 | Wilson et al. |
| 2008/0118214 | A1* | 5/2008 | Chen ..................... G02B 6/022 |
| | | | 385/128 |
| 2012/0215073 | A1 | 8/2012 | Sherman et al. |
| 2013/0267888 | A1 | 10/2013 | Rhodes et al. |
| 2014/0088371 | A1 | 3/2014 | Vayser et al. |
| 2016/0022146 | A1* | 1/2016 | Piron ................... A61B 5/0059 |
| | | | 600/411 |
| 2016/0089547 | A1 | 3/2016 | Shimizu et al. |
| 2016/0331646 | A1 | 11/2016 | Thomas |
| 2017/0273565 | A1 | 9/2017 | Ma et al. |
| 2018/0210126 | A1 | 7/2018 | Bauco |
| 2020/0030473 | A1 | 1/2020 | Sugimoto et al. |
| 2020/0061388 | A1* | 2/2020 | Yun ................... G02B 6/02033 |
| 2020/0206460 | A1 | 7/2020 | Mato et al. |

FOREIGN PATENT DOCUMENTS

| JP | 06-80439 U | 11/1994 |
| JP | 08-215316 | 8/1996 |
| JP | 2004-318090 | 11/2004 |
| JP | 2004-536639 | 12/2004 |
| JP | 2008-224979 | 9/2008 |
| JP | 2013-502280 | 1/2013 |
| JP | 2013-198644 | 10/2013 |
| JP | 2015-077168 | 4/2015 |
| JP | 2015-077336 | 4/2015 |
| JP | 2015-119837 | 7/2015 |
| JP | 2016-067526 | 5/2016 |
| JP | 2018-020091 | 2/2018 |
| JP | 2018-029753 | 3/2018 |
| JP | 2018-089004 | 6/2018 |
| JP | 2019-515718 | 6/2019 |
| WO | 02/103409 | 12/2002 |
| WO | 2013/171870 | 11/2013 |
| WO | 2015/133119 | 9/2015 |
| WO | 2017/141858 | 8/2017 |
| WO | 2018/207752 | 11/2018 |

OTHER PUBLICATIONS

Extended European Search Report issued in corresponding European Patent Application No. 20850704.6, Jun. 28, 2023, 8 pages.
Office Action issued in corresponding Chinese Patent Application No. 202080053707.2, Apr. 10, 2024, 15 pages w/translation.

* cited by examiner

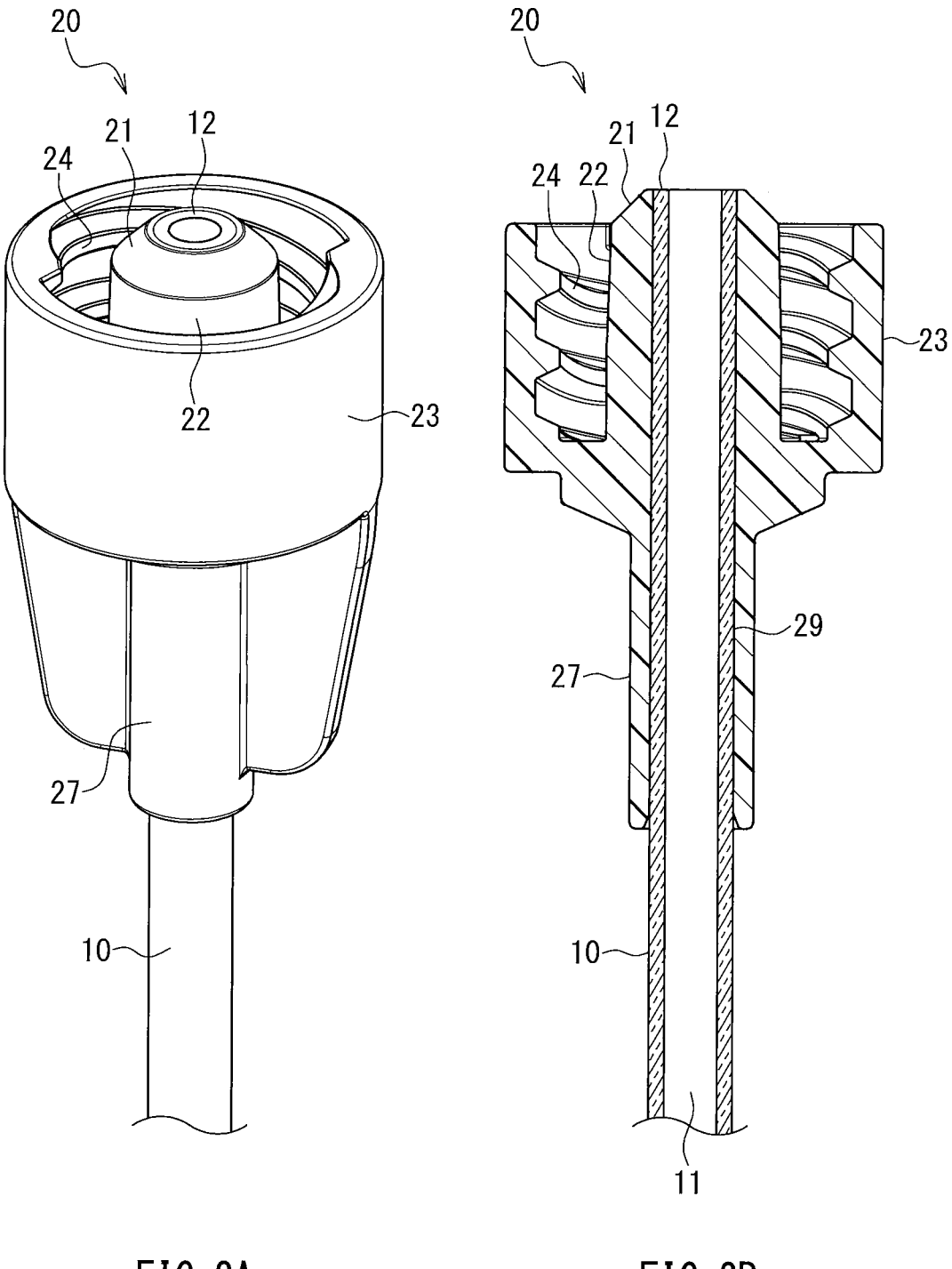
FIG. 2A                    FIG. 2B

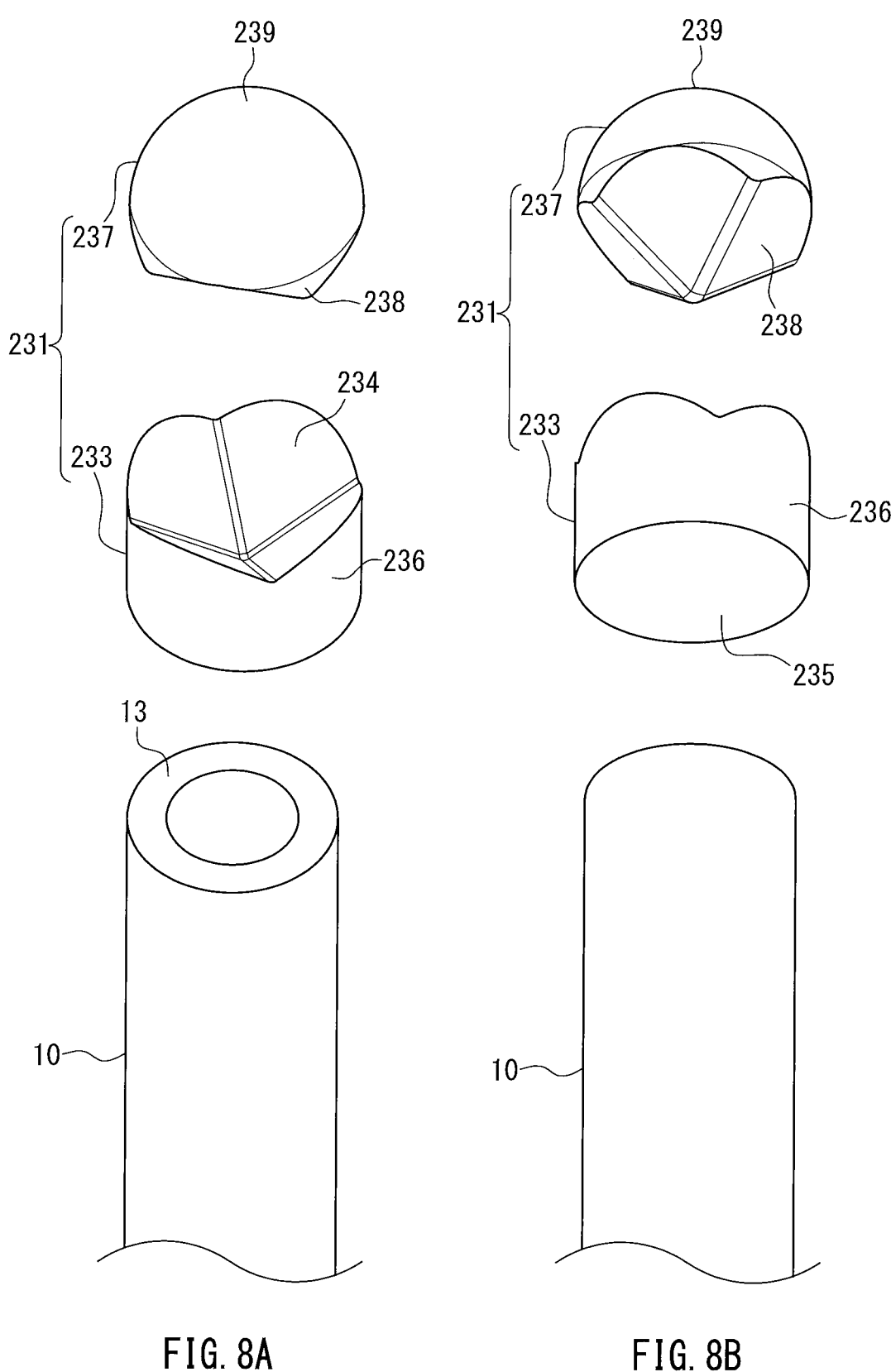
FIG. 8A                    FIG. 8B

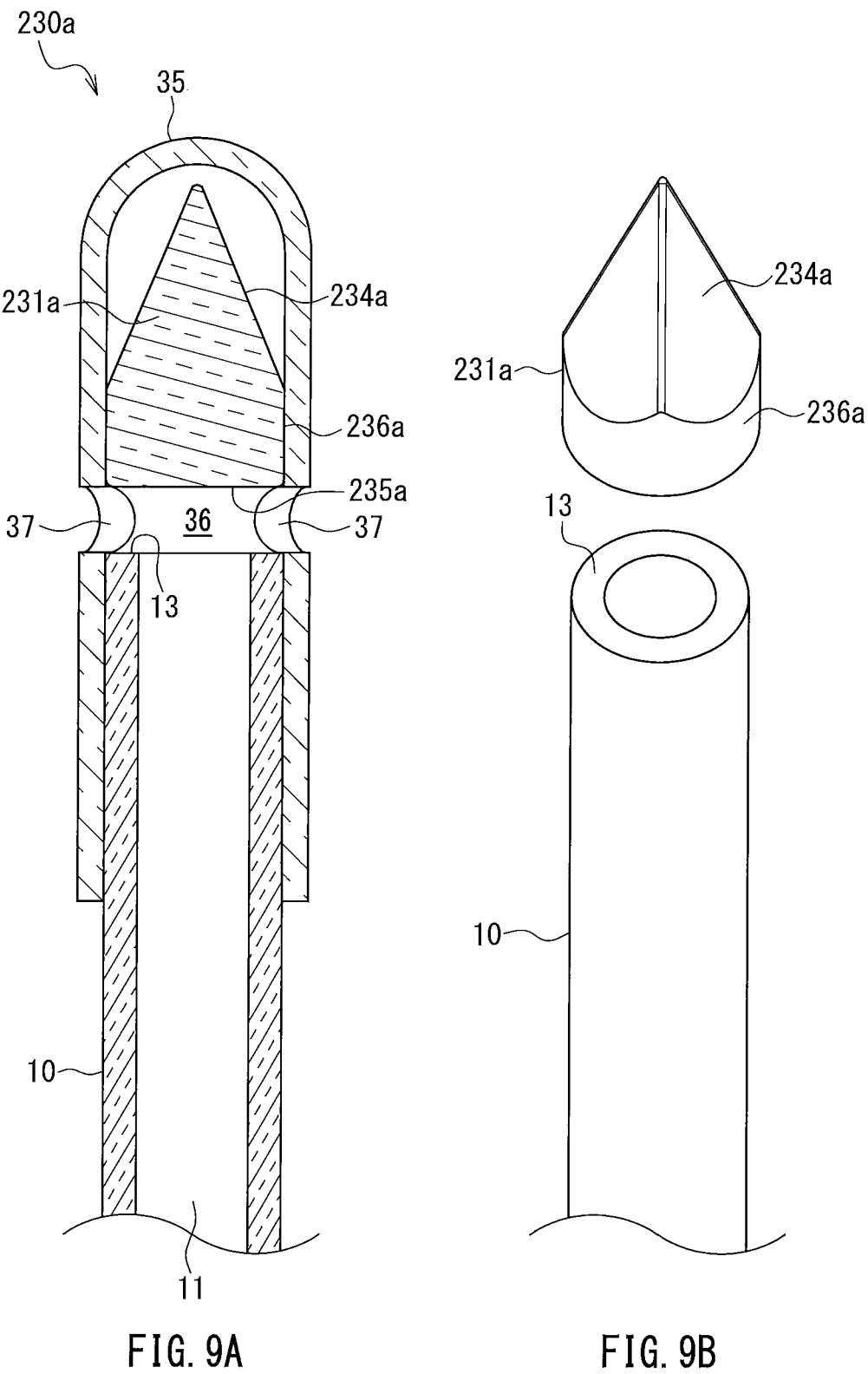
FIG. 9A                    FIG. 9B

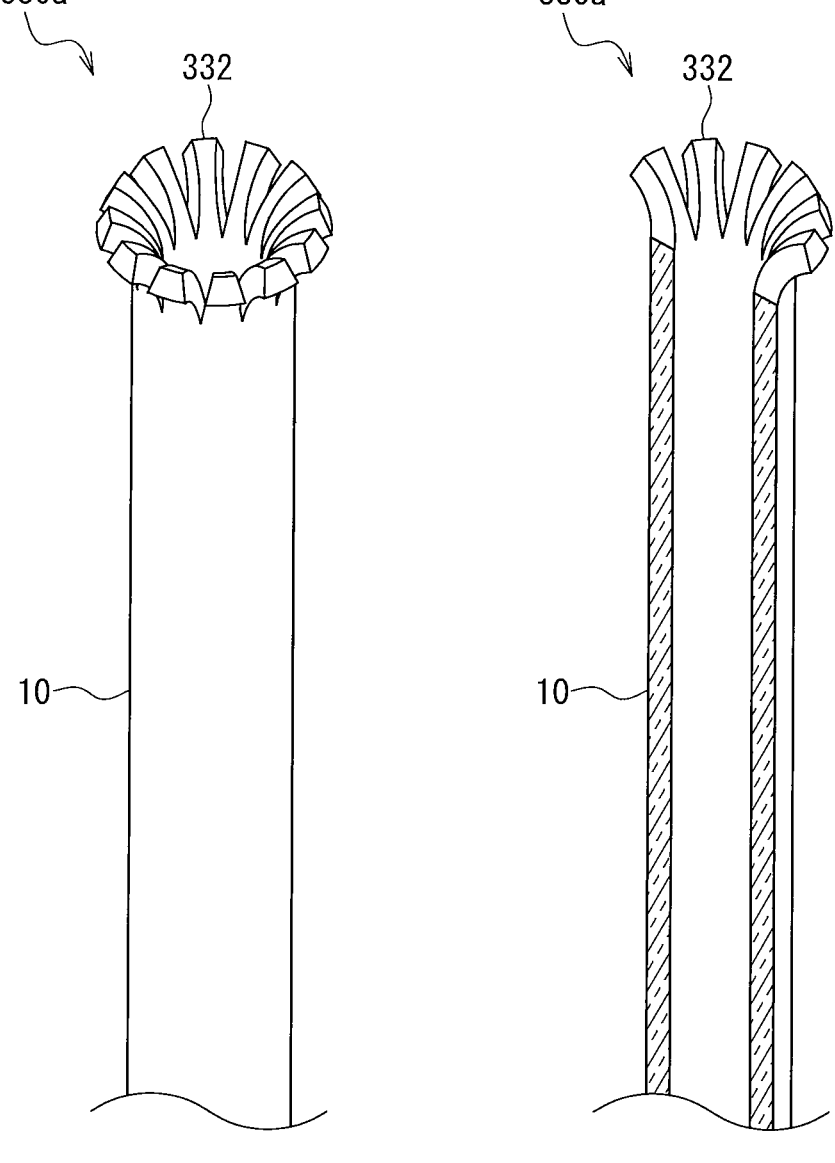
FIG. 12A                    FIG. 12B

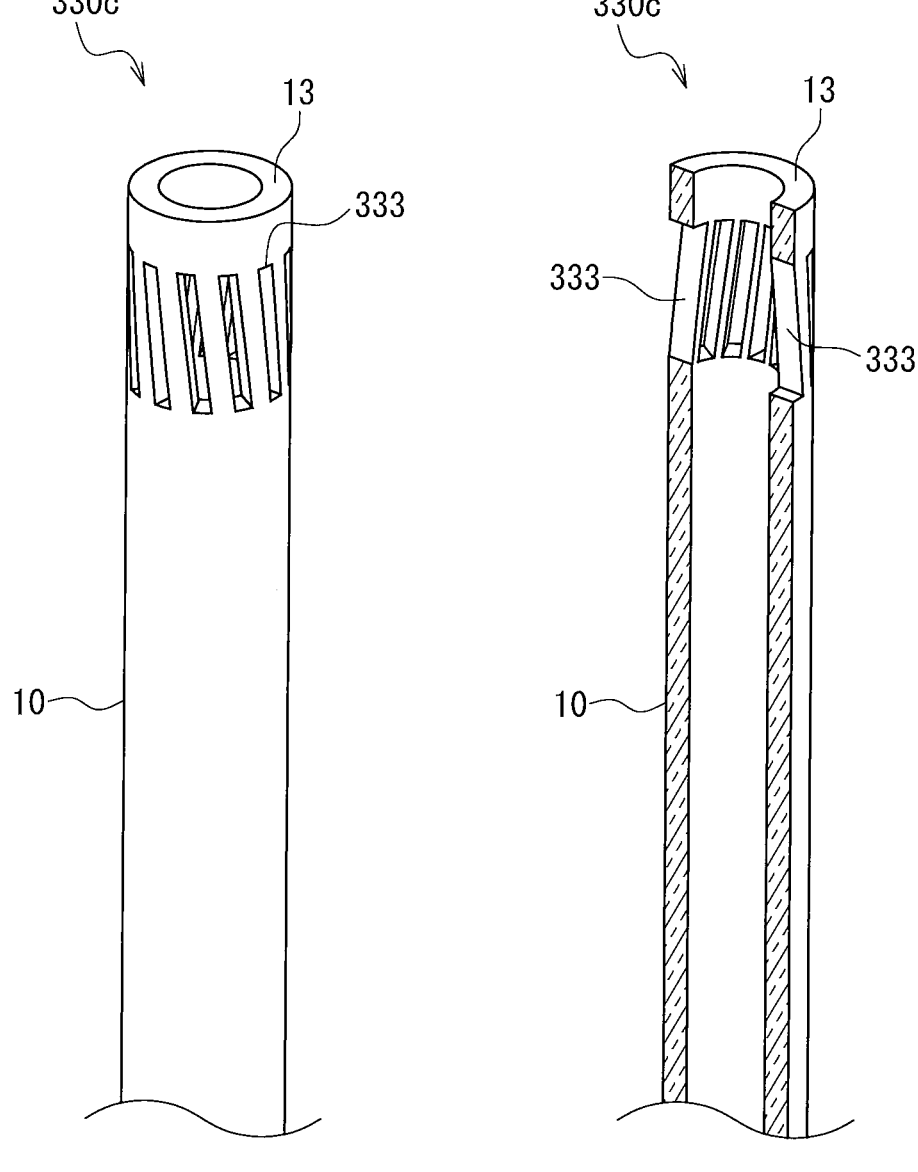
FIG. 14A                    FIG. 14B

SYSTEM FOR DETECTING POSITION OF DISTAL END OF MEDICAL TUBE

TECHNICAL FIELD

The present invention relates to a system for detecting the position of a distal end of a tube inserted into a human body.

BACKGROUND ART

In clinical medicine, tube feeding, in which various medical tubes are inserted into the patient's body cavity for treatment, is widely used. For example, in order to supply a liquid nutrient from the outside to a patient who has difficulty in chewing or swallowing, oral or nasal tube feeding is used in which the nutrient is delivered directly to the stomach via a medical tube (called an oral or nasal tube, and hereinafter referred to simply as "tube") inserted through the mouth or nose.

When oral or nasal tube feeding is used, a distal end of the tube needs to be securely positioned in the stomach. Incorrect insertion of the tube into the trachea or bronchus is extremely dangerous. It is necessary to accurately confirm the position of the distal end of the tube in the patient's body.

X-ray fluoroscopy is the most reliable method to confirm the position of the distal end of the tube. However, it requires the patient to be moved to an X-ray machine for confirmation, which places a heavy physical burden on the patient. The tube will remain indwelling in the patient for several days. During this period, the distal end of the tube may move due to cough reflex or vomiting. For this reason, it is necessary to check the position of the distal end at predetermined time intervals. If X-ray fluoroscopy is performed each time, the burden on the patient increases further, and the amount of X-ray exposure also increases.

A method of measuring the pH of a liquid aspirated through the tube to determine whether or not the distal end of the tube is in the stomach is sometimes used. However, this method is less reliable for patients with suppressed gastric acid secretion.

Patent Document 1 discloses a method of confirming the position of the distal end of the tube by inserting a tube with an optical fiber inserted into the tube beforehand into the patient and observing the light radiated from a distal end of the optical fiber from outside the body. This method is simple, and the patient burden is low.

However, in order to deliver a nutrient through the tube into the stomach, the optical fiber needs to be pulled out of the tube. Reinserting the optical fiber into the tube afterward can cause accidents such as the inserted optical fiber damaging the tube and the optical fiber protruding from the damaged part of the tube and damaging the wall of the digestive tract. For this reason, the method in Patent Document 1 can only be used for the initial insertion of the tube into the patient, and cannot be used for subsequent periodic checks of the position of the distal end of the tube.

CITATION LIST

Patent Documents

Patent Document 1: WO 2015/133119A1
Patent Document 2: JP 2015-119837A
Patent Document 2: JP 2018-029753A

DISCLOSURE OF INVENTION

Problem to be Solved by the Invention

An object of the present invention is to easily, accurately, and safely detect the position of the distal end of a tube inserted into a patient.

Means for Solving Problem

The present invention relates to a medical tube distal end position detection system for detecting a position of a distal end of a tube inserted into a patient. The system includes a light source device that emits light; a hollow tube having a flow path that allows a liquid to flow through; a connector provided at a base end of the tube so as to allow light from the light source device to be incident on an end surface at the base end of the tube; and a light emitting portion provided at the distal end of the tube. Light from the light source device is passed through the tube and emitted from the light emitting portion, and the light from the light emitting portion is transmitted to a body surface.

Effects of the Invention

According to the present invention, it is possible to easily, accurately, and safely detect the position of the distal end of a tube inserted into a patient.

BRIEF DESCRIPTION OF DRAWINGS

FIG. 2A is a perspective view of a connector according to Embodiment 1 of the present invention, and FIG. 2B is a cross-sectional view of the connector.

FIG. 8A is an exploded perspective view of the light emitting portion according to Embodiment 2 of the present invention as viewed from a distal end side, and FIG. 8B is an exploded perspective view of the light emitting portion as viewed from a base end side.

FIG. 9A is a cross-sectional view of another light emitting portion according to Embodiment 2 of the present invention, and FIG. 9B is an exploded perspective view of the light emitting portion as viewed from the distal end side.

FIG. 12A is a perspective view of another light emitting portion according to Embodiment 3 of the present invention, and FIG. 12B is a cross-sectional perspective view of the light emitting portion.

FIG. 14A is a perspective view of yet another light emitting portion according to Embodiment 3 of the present invention, and FIG. 14B is a cross-sectional perspective view of the light emitting portion.

DESCRIPTION OF THE INVENTION

Figure 1:
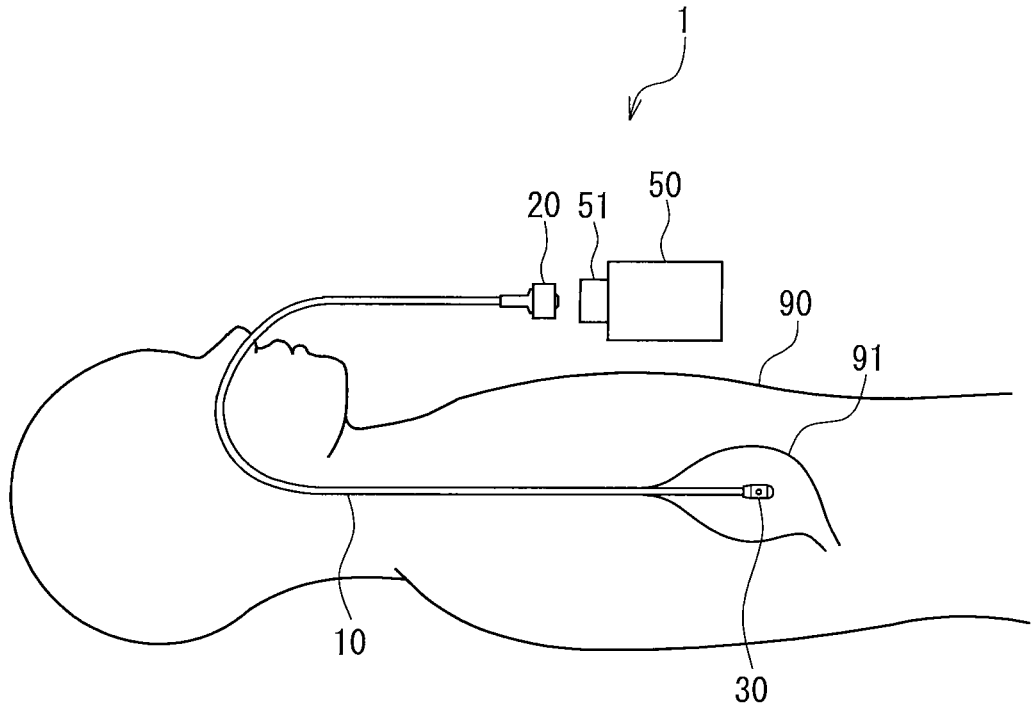
FIG. 1 shows a schematic configuration of a medical tube distal end position detection system according to Embodiment 1 of the present invention.

In the above-described system of the present invention, light emitted by the light source device may have a wavelength of 360 nm to 3,000 nm. Light having a wavelength within this range has a high transmittance through the human body and therefore makes it easy to detect the position of the distal end of the tube. Also, light having a wavelength within this range is minimally invasive to the human body and is therefore highly safe.

The connector may have a cylindrical male member into which the tube is inserted, an outer cylinder surrounding the male member, and a female thread formed on an inner circumferential surface of the outer cylinder that opposes the male member. With this configuration, oral or nasal tube feeding can be performed using the tube with the connector of the present invention, instead of a conventional oral or nasal tube. Since the tube is inserted into the male member, it is easy to allow light from the light source device to be incident on the end surface at the base end of the tube.

The end surface at the base end of the tube may be exposed at an opening at a leading end of the male member. This configuration is advantageous for allowing light from the light source device to be incident on the end surface at the base end of the tube.

The light emitting portion may include a reflective member that reflects light emerging from the tube. The reflective member reflects light emerging from the tube in various directions, including a radial direction (direction that is perpendicular to a longitudinal direction of the tube). Thus, it is easy to observe light from the light emitting portion on the body surface of the patient irrespective of the orientation of the light emitting portion in the patient's body.

The reflective member may have a spherical surface or a pyramidal or conical surface on a side thereof that opposes an end surface at the distal end of the tube. In this case, light emerging from the tube can be reflected in various directions, including the radial direction, with a simple configuration.

The reflective member may be made of titanium. Titanium has excellent anticorrosion properties and biocompatibility, and therefore, this configuration is advantageous for maintaining good light reflection characteristics for a long period of time.

The reflective member may be provided in direct contact with the tube. This configuration is advantageous for simplifying the configuration of the light emitting portion and facilitating the production of the tube provided with the light emitting portion. With this configuration, the housing can be omitted from the light emitting portion.

The reflective member may be a metal vapor deposition layer. With this configuration, it is possible to provide the reflective member on the tube with ease.

The light emitting portion may include a refractive member that refracts light emerging from the tube. The refractive member refracts light emerging from the tube in various directions, including the radial direction. Thus, it is easy to observe light from the light emitting portion on the body surface of the patient irrespective of the orientation of the light emitting portion in the patient's body.

The light emitting portion may include the distal end of the tube that is formed so that light that has passed through the tube emerges therefrom while being refracted. With this configuration, light that has passed through the tube emerges from the tube while being refracted in various directions, including the radial direction. Thus, it is easy to observe light from the light emitting portion on the body surface of the patient irrespective of the orientation of the light emitting portion in the patient's body.

The light emitting portion may include a hole extending through the tube or a recess formed on an inner surface or an outer surface of the tube. With this configuration, light that has passed through the tube is refracted by the hole or the recess and emerges from the tube in various directions, including the radial direction. Thus, it is easy to observe light from the light emitting portion on the body surface of the patient irrespective of the orientation of the light emitting portion in the patient's body.

A leaked light prevention layer for preventing leaked light from an outer surface of the tube may be provided on the outer surface of the tube. The leaked light prevention layer may be removed from the light emitting portion. With this configuration, light that has passed through the tube is refracted and emerges in various directions, including the radial direction, from a region where the leaked light prevention layer has been removed. Thus, light from the light emitting portion can be observed on the body surface of the patient, irrespective of the orientation of the light emitting portion in the patient's body, using a simple method.

The light emitting portion may have a housing. The housing may have a hole that allows the liquid that has flowed through the tube to flow out to an outside. With this configuration, the liquid that has flowed through the flow path of the tube can be administered to the patient via the hole in the housing. Also, the reflective member or the refractive member can be retained in a desired position relative to an end surface at the distal end of the tube by using the housing.

The light emitting portion may have a translucent or transparent housing. With this configuration, light loss when light emerging from the distal end of the tube passes through the housing is reduced. This is advantageous for ensuring the brightness of the light emitting portion, and facilitates the detection of the position of the distal end of the tube.

The outer surface of the tube may have a surface roughness Ra of 1.2 μm or less. With this configuration, light loss when light passes through the tube is reduced. This is advantageous for ensuring the brightness of the light emitting portion, and facilitates the detection of the position of the distal end of the tube.

An outer surface of the tube may be covered by a coating material having a lower refractive index than the tube. With this configuration, light loss when light passes through the tube is reduced. This is advantageous for ensuring the brightness of the light emitting portion, and facilitates the detection of the position of the distal end of the tube.

The system of the present invention may further have a stylet or an optical fiber that can be removably inserted into the flow path of the tube. The stylet and the optical fiber improve the ease of insertion of the tube. Also, the stylet makes it possible to confirm the position of the tube using X-ray fluoroscopy. The optical fiber improves the brightness of the light emitting portion and facilitates the detection of the position of the distal end of the tube.

Hereinafter, the present invention will be described in detail while showing preferred embodiments thereof. However, it goes without saying that the present invention is not limited to the embodiments below. In the drawings that will be referred to in the following description, only the main members of constituent members of the embodiments of the present invention are shown in a simplified manner for the sake of convenience of description. Accordingly, the present invention may include optional members that are not shown in the drawings below. Also, the members shown in the drawings below may be changed or omitted within the scope of the present invention. In the drawings that will be referred to in the description of the embodiments below, members corresponding to those members shown in the drawings that are referred to in the description of any preceding embodiment are denoted by the same reference numerals as the reference numerals of the members shown in the drawings of that preceding embodiment. With respect to such members, redundant descriptions are omitted, and the description of the preceding embodiment should be taken into account.

Embodiment 1

FIG. 1 shows a schematic configuration of a system 1 according to Embodiment 1 of the present invention that is applied to oral or nasal tube feeding. An oral or nasal tube (hereinafter referred to simply as "tube") 10 is inserted through the nasal cavity of a patient 90, and a distal end thereof reaches the stomach 91. The tube 10 is flexible so that it can be bent and deformed. The tube 10 is a hollow cylindrical object in which a continuous flow path 11 (see FIGS. 2B and 3B, which will be described later) is formed over the entire length thereof. A liquid such as a nutrient is administered to the stomach 91 of the patient through the flow path 11. A connector 20 is provided at a base end of the tube 10. A light emitting portion 30 is provided at the distal end of the tube 10. The connector 20 can be repeatedly connected to and disconnected from a light source device 50. When the connector 20 is connected to the light source device 50, light from a light source (not shown) incorporated in the light source device 50 passes through the tube 10 and is emitted from the light emitting portion 30. The light from the light emitting portion 30 is transmitted through the body of the patient 90 and causes the body surface to glow. An operator can confirm the position of the distal end of the tube 10 based on the light emitting position on the body surface of the patient 90.

FIG. 2A is a perspective view of the connector 20, and FIG. 2B is a cross-sectional view of the connector 20. The connector 20 is a male connector including a male member 21 that has a cylindrical shape. An outer circumferential surface 22 of the male member 21 is a tapered surface (so-called male tapered surface) whose outer diameter gradually decreases toward a leading end of the male member 21. An outer cylinder 23 having a cylindrical shape is arranged coaxially with the male member 21. The outer cylinder 23 is provided spaced apart from the male member 21 in the radial direction and surrounds the male member 21. A female thread 24 is provided on an inner circumferential surface of the outer cylinder 23 that opposes the male member 21. The leading end of the male member 21 protrudes from a leading end of the outer cylinder 23. A cylindrical base cylinder 27 extends coaxially with the male member 21 in a direction opposite to the male member 21. A through hole 29 extends through the connector 20 from the leading end of the male member 21 to a leading end of the base cylinder 27. The tube 10 is inserted into the through hole 29 from the base cylinder 27 to the male member 21. A flat end surface 12 is formed at the base end of the tube 10. The end surface 12 is perpendicular to the longitudinal direction of the tube 10. The end surface 12 is exposed at an opening at the leading end of the male member 21 and constitutes a flat surface that is coplanar with a leading end surface of the male member 21. The tube 10 is fixed to the connector 20 at a position of, for example, the base cylinder 27 through adhesion or the like to an inner surface of the through hole 29.

The connector 20 (in particular, the outer circumferential surface 22 of the male member 21 and the female thread 24) is configured to be compatible with a male connector (see Patent Documents 2 and 3, for example) that is provided at the base end of an oral or nasal tube commonly used for oral or nasal tube feeding. Accordingly, oral or nasal tube feeding can be performed using the tube 10 with the connector 20, instead of a conventional oral or nasal tube.

The connector 20 is made of a material that is hard (hard material), and has such a mechanical strength (stiffness) that it will not be substantially deformed by an external force. Specifically, although the material of the connector 20 is not limited, it is possible to use, for example, resins such as polypropylene (PP), polycarbonate (PC), polyacetal (POM), polystyrene, polyamide, polyethylene, hard polyvinyl chloride, and ABS (acrylonitrile-butadiene-styrene copolymer). The entire connector 20 can be integrally produced as a single component through injection molding or the like using such a resin.

Figures 3A, 3B:
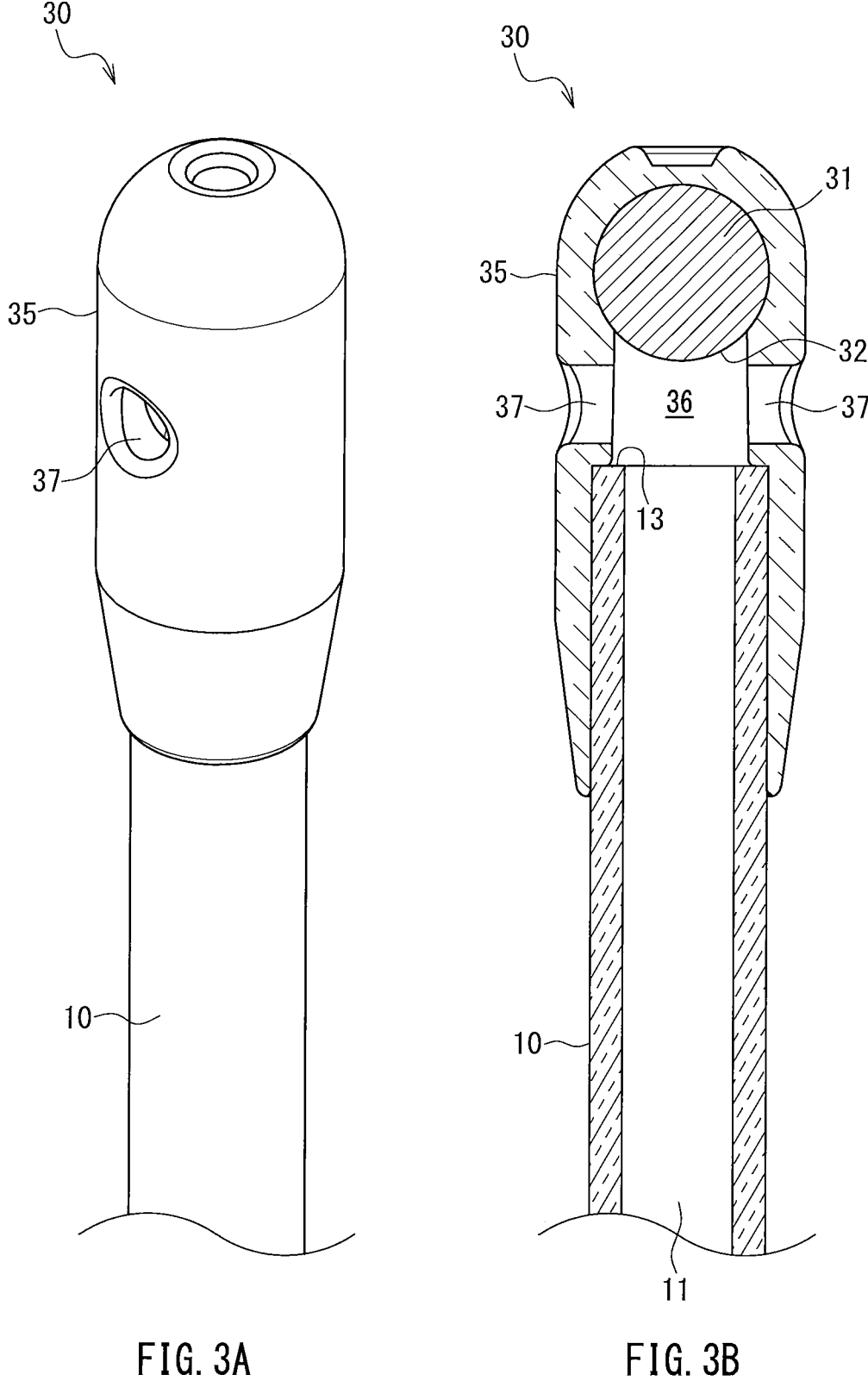
FIG. 3A is a perspective view of a light emitting portion according to Embodiment 1 of the present invention.
FIG. 3B is a cross-sectional view of the light emitting portion.

FIG. 3A is a perspective view of the light emitting portion 30, and FIG. 3B is a cross-sectional view of the light emitting portion 30. The light emitting portion 30 has a reflective member 31 and a housing 35. The entire housing 35 has a hollow artillery shell shape in which one end (distal end) thereof in the longitudinal direction bulges into a dome shape (hemispherical shape) and the other end (base end) is open. The distal end of the tube 10 is inserted into the opening of the housing 35. The housing 35 is liquid-tightly fixed to the tube 10 through adhesion or the like. The reflective member 31 has a spherical shape and is accommodated in an innermost portion of an inner cavity 36 of the housing 35. A flat end surface 13 is formed at the distal end of the tube 10. The end surface 13 is perpendicular to the longitudinal direction of the tube 10. The reflective member 31 opposes the end surface 13 and is spaced apart from the end surface 13. The center of the reflective member 31 is located on a central axis of the tube 10. Although the outer diameter of the reflective member 31 is not limited, it is preferable that the outer diameter is equal to or slightly larger than the outer diameter of the tube 10. Light that has passed through the tube 10 and emerged from the end surface 13 is reflected by a spherical surface 32 of the reflective member 31 and passes through the housing 35.

The housing 35 has a hole (side hole) 37 extending through the housing 35 in the radial direction. Here, the term "radial direction" means the direction of a straight line that is orthogonal to the central axis, which passes through the center of the reflective member 31, of the tube 10. The hole 37 brings the inner cavity 36 of the housing 35 and the outside of the housing 35 into communication with each other at a position between the end surface 13 and the reflective member 31. In Embodiment 1, two holes 37 are provided; however, the number of holes 37 may also be one or three or more.

The reflective member 31 can be made of a non-translucent material. Although there is no limitation on the non-translucent material, a metal such as titanium, stainless steel, a cobalt alloy, aluminum, or iron is preferable. Titanium, stainless steel, and a cobalt alloy have excellent anticorrosion properties and biocompatibility and can maintain good light reflection characteristics for a long period of time. Of these, titanium is most preferable. Stainless steel, aluminum, and iron are inexpensive. Titanium, aluminum, and the like are non- or low-magnetic materials and are therefore unlikely to be attracted during MRI scans. The spherical surface 32 of the reflective member 31 is preferably glossy, and particularly preferably mirror-finished, so as to function as a reflective surface that reflects light emerging from the end surface 13. The reflective member 31 can also serve as a weight for facilitating the insertion of the tube 10 into the digestive tract. In order to ensure that a distal end portion of the tube 10 has a required load, the housing 35 may also accommodate another weight separate from the reflective member 31. In this case, the other weight is arranged on the opposite side of the reflective member 31 from the end surface 31.

The reflective member 31 may be made of a translucent or transparent material. Even a translucent or transparent material can be used as the reflective member 31 as long as it can reflect at least a portion of light emerging from the end surface 13. The translucent or transparent material may be plastic, glass, or the like. Plastic and glass are materials with low electrical conductivity, and therefore do not cause burns and the like due to heat generation during MRI scans. The surface of the translucent or transparent material may be processed (reflective processing) so as to reflect light. Examples of the reflective processing include, but are not limited to, various types of coating, satin finishing, metal vapor deposition, mirror finishing, and the like. The reflective member 31 may also be a mirror.

A portion of light incident on the reflective member 31 may be reflected by the surface of the reflective member 31, and the remaining light may enter the reflective member 31. In this case, the light may also be refracted when entering the reflective member 31 and when emerging from the reflective member 31. That is to say, the reflective member 31 may also function as a refractive member (see Embodiment 2, which will be described later).

Although there is no limitation on the material of the housing 35, a translucent or transparent and flexible material is preferable, and, for example, a resin such as polyurethane, polyethylene, silicone, acrylic, or polypropylene can be used.

Although there is no limitation on the material of the tube 10, a translucent or transparent and flexible material is preferable, and, for example, a resin such as polyurethane, acrylic, silicone, polyethylene, a styrene elastomer, or polybutadiene can be used.

In Embodiment 1, light entering from the end surface 12 (see FIG. 2B) at the base end passes through the tube 10 (a portion between an inner surface and an outer surface of the tube 10, the portion constituting the thickness of the tube 10; hereinafter this portion will be referred to as a "thickness portion of the tube 10") and emerges from the end surface 13 (see FIG. 3B) at the distal end, and thus, the light emitting portion 30 emits light. In order to ensure the brightness (luminous flux) of the light emitting portion 30, it is preferable to reduce light loss between the end surfaces 12 and 13. For this purpose, it is effective to reduce light (leaked light) emerging to the outside from the outer surface of the tube 10 between the end surfaces 12 and 13. Although there is no limitation on the means for reducing leaked light, for example, one of, or a combination of two or more of, the following techniques can be used: (1) smoothing the outer surface of the tube 10; (2) covering the outer surface of the tube 10 with a coating material having a lower refractive index than the tube 10; (3) providing a metal vapor deposition layer made of silver, aluminum, or the like on the outer surface of the tube 10; (4) forming a tube 10 having a two-layer structure constituted by a layer with a high refractive index and a layer with a low refractive index; and so on.

With regard to (1) above, the surface roughness Ra of the outer surface of the tube 10 is preferably 1.2 μm or less, more preferably 1.0 μm or less, and particularly preferably 0.4 μm or less. Although there is no limitation on the method for smoothing the outer surface of the tube 10, for example, a method can be adopted in which, when extruding a resin material for the tube 10 from a nozzle, the temperature of the nozzle is set to be higher than usual.

With regard to (2) above, although depending on the material of the tube 10, examples of the coating material that covers the outer surface of the tube 10 include a silicon oil, fluorine, an UV-curable material with a low refractive index, and the like. These materials have a lower refractive index than the above-described resin material constituting the tube 10, and thus, light emerging from the inside of the tube 10 to the coating material layer is reduced. Although there is no limitation on the method for covering the outer surface of the tube 10 with fluorine, examples thereof include applying liquid fluorine to the outer surface of the tube 10; spraying a fluorine gas onto the outer surface of the tube 10; and the like.

With regard to (4) above, a tube 10 having a two-layer structure can be produced by coextruding two layers using two types of materials having different refractive indices such that the material having the high refractive index forms the inner layer and the material having the low refractive index forms the outer layer. Alternatively, the tube 10 may have a three-layer structure constituted by inner and outer layers that have a low refractive index and an intermediate layer that is provided between the inner and outer layers and has a high refractive index. The tube 10 may also have another multi-layer structure (e.g., a five-layer structure). In each case, light passes through a high refractive index layer.

In order to ensure the brightness (luminous flux) of the light emitting portion 30, it is also effective to reduce light loss at the end surfaces 12 and 13 of the tube 10. For this purpose, it is preferable that the end surfaces 12 and 13 are smooth, or more specifically, the surface roughness Ra of the end surfaces 12 and 13 is preferably 1.2 μm or less, more preferably 1.0 μm or less, and particularly preferably 0.4 μm or less. End surfaces 12 and 13 that are smooth as described above can be obtained by, for example, polishing the end surfaces 12 and 13.

Referring again to FIG. 1, the light source device 50 has the light source (not shown) that emits light. It is preferable that the light is visible light or near-infrared light. Although there is no limitation on the wavelength of the light, it is preferable that the wavelength of the light is 360 nm or more, and more preferably 630 nm or more, and is 3,000 nm or less, and more preferably 780 nm or less. Light having a wavelength within this range has a high transmittance through the human body, and is also minimally invasive to the human body and hence highly safe. Since visible light can be observed with the naked eye, the position of the light emitting portion 30 can be confirmed with ease. Near-infrared light has superior translucency to that of visible light and can be observed via a dedicated camera such as an infrared camera. With use of a camera, it is easy to keep a captured image (either a still image or a moving image) for record purposes. Specifically, light having a wavelength of 630 nm can be used as visible light, and light having a wavelength of 780 nm can be used as near-infrared light. Alight emitting diode (LED) can be used as the light source. The light source device 50 has a socket (insertion port) 51 to which the connector 20 can be removably attached. The light source is arranged so as to oppose the end surface 12 of the tube 10 when the connector 20 is connected to the socket 51. The light source may be provided with a lens so that light can be efficiently incident on the end surface 12. The socket 51 may include a switch (not shown) for turning on/off the light emission of the light source in conjunction with the attachment/removal of the connector 20 to/from the socket 51. This is advantageous for reliably preventing light emitted by the light source device 50 from entering the eyes of the operator or the patient when the connector 20 is not connected. The light source device 50 may include a plurality of sockets 51, and in this case, the plurality of sockets 51 may include respective light sources that emit light with different wavelengths. For example, a first socket may include a light source that emits light with a wavelength of 630 nm, and a second socket may include a light source that emits light with a wavelength of 780 nm. Alternatively, a configuration may be adopted in which a single socket 51 includes a plurality of light sources that emit light with different wavelengths (e.g., a first light source that emits light with a wavelength of 630 nm and a second light source that emits light with a wavelength of 780 nm) such that switching between the plurality of light sources is possible. A power source for the light source device 50 may be either a commercial power source or a battery (including a storage battery). In the case where a battery is used as the power source, it is easy to improve the portability of the light source device 50 and reduce the size and weight of the light source device 50.

A method of using the system 1 of Embodiment 1 will be described.

Like a common oral or nasal tube, the tube 10 is inserted into the nasal cavity of the patient 90. The connector 20 is connected to the light source device 50, and then, the light emitting portion 30 emits light. The light from the light emitting portion 30 is transmitted through the human body. The operator can confirm the position of the light emitting portion 30 based on the light emitting position on the body surface of the patient 90. Light can be observed with the naked eye depending on its wavelength. If necessary, the light emitting position may be confirmed by capturing an image with an infrared camera. The connector 20 may be connected to the light source device 50 before the tube 10 is inserted into the patient 90 or may be connected to the light source device 50 at the time when the light emitting portion 30 is considered to have reached the stomach.

The tube 10 with a stylet inserted into its flow path 11 beforehand may also be inserted into the patient 90. Abase end of the stylet can be led out through the connector 20. In this case, the connector 20 is connected to the light source device 50 after the stylet is pulled out of the tube 10.

The tube 10 with an optical fiber inserted into its flow path 11 such that a distal end of the optical fiber reaches the light emitting portion 30 may also be inserted into the patient 90. In addition to the light emitting portion 30, the distal end of the optical fiber is also made to emit light using the light source device 50. Thus, the luminous flux from the light emitting portion 30 increases, and therefore the position of the light emitting portion 30 can be confirmed with higher accuracy. The optical fiber is pulled out of the tube 10 after it is confirmed that the distal end of the tube 10 has reached the stomach.

Compared with a case in which the tube 10 is used alone, when the stylet or the optical fiber is inserted into the tube 10, the flexural modulus of elasticity and the strength of the tube 10 increase, and the ease of insertion of the tube 10 into the human body improves accordingly. It is preferable that the stylet and the optical fiber have a higher flexural modulus of elasticity than the tube 10. A stylet or an optical fiber having a higher flexural modulus of elasticity than the tube 10 can be more easily assembled to the tube 10 than those having a lower flexural modulus of elasticity than the tube 10.

During the initial insertion of the tube 10 into the patient, X-ray fluoroscopy may be used at the same time in order to more accurately confirm the position of the tube 10. It is known that halides can be observed under X-ray fluoroscopy. The tube 10 can contain a halide. Specifically, the outer surface of the tube 10 may be coated with a halide; a halide may be kneaded into a material constituting the tube 10; a halide may be polymerized into a resin constituting the tube 10; or other methods may be used. In such a manner, X-ray contrast properties can be imparted to the tube 10. In the case where an optical fiber is inserted into the tube 10, X-ray contrast properties may be imparted to the optical fiber by making the optical fiber contain a halide using a method similar to any of the above-described methods. A stylet includes a thin metal wire and has X-ray contrast properties. For this reason, in the case where a stylet is inserted into the tube 10, there is no necessity to impart X-ray contrast properties to the tube 10.

After it is confirmed that the distal end (i.e., the light emitting portion 30) of the tube 10 has reached the stomach, the connector 20 is connected to a connector (female connector) provided at a downstream end of a tube for conveying the nutrient (see FIG. 16A of Patent Document 3, for example). The nutrient flows through the flow path 11 of the tube 10 and is administered to the patient via the hole 37 in the housing 35.

The tube 10 will remain in the patient 90 for several days. During this period, the light emitting portion 30 may move due to the tube 10 curling up, for example. To address this issue, the connector 20 is connected to the light source device 50 at predetermined time intervals (e.g., immediately before administration of the nutrient to the patient 90) to cause the light emitting portion 30 to emit light, and the position of the light emitting portion 30 is thereby confirmed.

As described above, according to Embodiment 1, the light emitting portion 30 provided at the distal end of the tube 10 is made to emit light, and the light from the light emitting portion 30 is observed through the body of the patient 90. Thus, it is possible to easily and accurately detect the position of the distal end of the tube 10. Unlike X-rays, light emitted from the light emitting portion 30 is highly safe.

Since the reflective member 31 reflects light emerging from the end surface 13 in various directions, light from the light emitting portion 30 can be observed on the body surface of the patient 90 irrespective of the orientation of the light emitting portion 30.

In Patent Document 1 above, in order to confirm the position of the distal end of the tube, it is necessary to insert an optical fiber into the tube. In order to confirm the position of the distal end of the tube again after the tube 10 has been inserted into the patient and the optical fiber has been pulled out, it is necessary to re-insert the optical fiber into the tube. This can lead to an accident of the optical fiber piercing the tube and damaging the wall of the digestive tract. By contrast, in Embodiment 1, the tube 10 itself serves as a light transmission path, and the light emitting portion 30 is provided at the distal end of the tube 10. The optical fiber that is essential in Patent Document 1 is not necessary in Embodiment 1. Therefore, in Embodiment 1, the aforementioned accident that may occur in Patent Document 1 cannot occur. After the tube 10 has been inserted into the patient 90, the position of the distal end of the tube 10 can be confirmed at any time. The system 1 of Embodiment 1 is highly safe.

In Embodiment 1, the tube 10 itself functions as a light-guiding member, and therefore, it is not necessary to provide a light-guiding member, such as an optical fiber, separate from the tube 10. Thus, the system 1 of Embodiment 1 has a simple configuration and is inexpensive.

In the above-described embodiment, the light emitting portion 30 includes the spherical reflective member 31, and light emerging from the end surface 13 is reflected by the spherical surface 32 of the reflective member 31. However, the reflective member of the present invention is not limited to this.

Figures 4A, 4B:
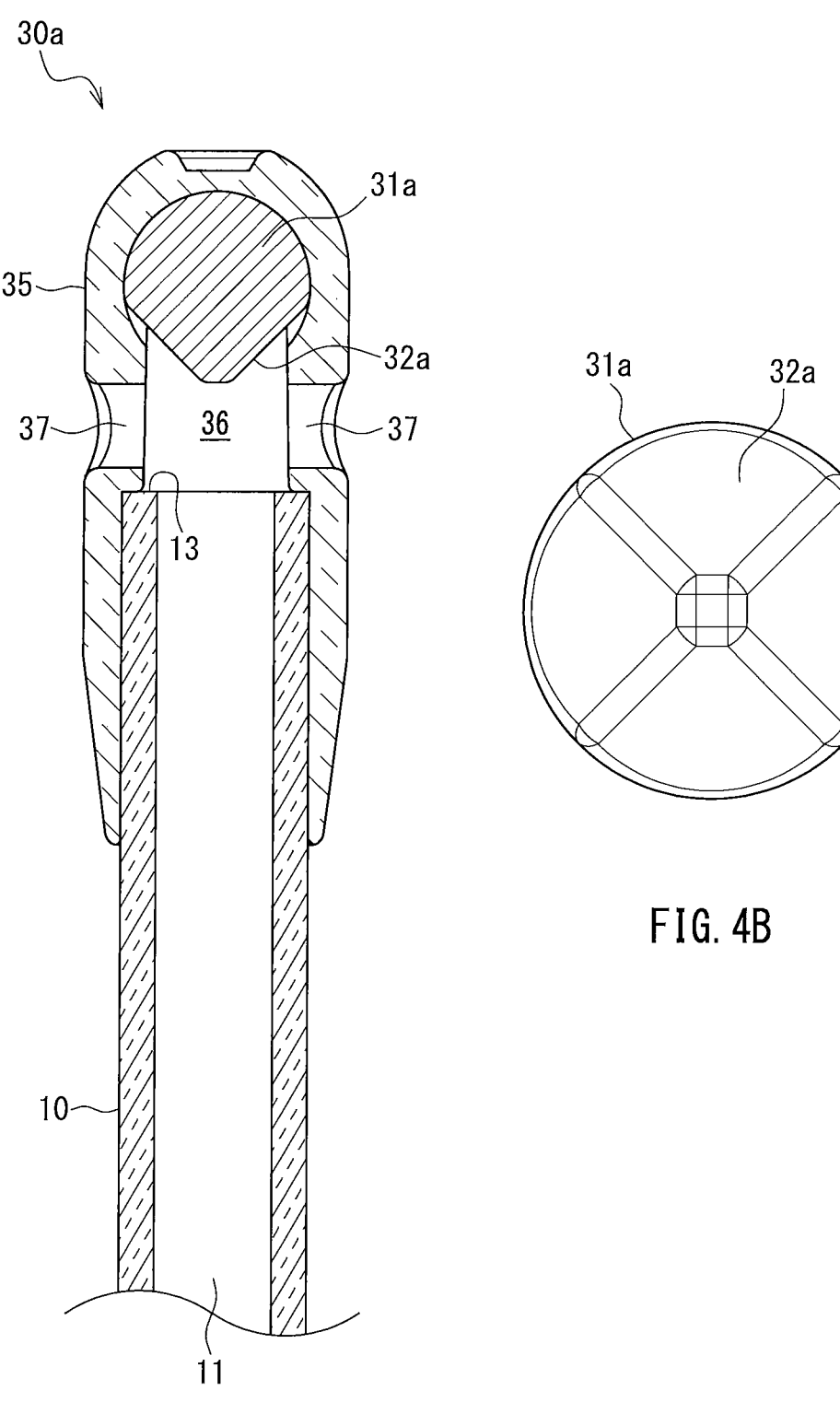
FIG. 4A is a cross-sectional view of another light emitting portion according to Embodiment 1 of the present invention.
FIG. 4B is a front view of a reflective surface of a reflective member of the light emitting portion.

For example, as shown in FIGS. 4A and 4B, a light emitting portion 30a may include a reflective member 31a that has a quadrangular pyramidal surface 32a as a reflective surface. The quadrangular pyramidal surface 32a is arranged coaxially with the tube 10 such that it is spaced apart from the end surface 13 and opposes the end surface 13. Light emerging from the end surface 13 is reflected by the quadrangular pyramidal surface 32a and passes through the housing 35. Instead of the quadrangular pyramidal surface 32a, the reflective member 31a may have any pyramidal surface (preferably, a regular pyramidal surface), such as a triangular pyramidal surface, a pentagonal pyramidal surface, or the like.

Figures 5A, 5B:
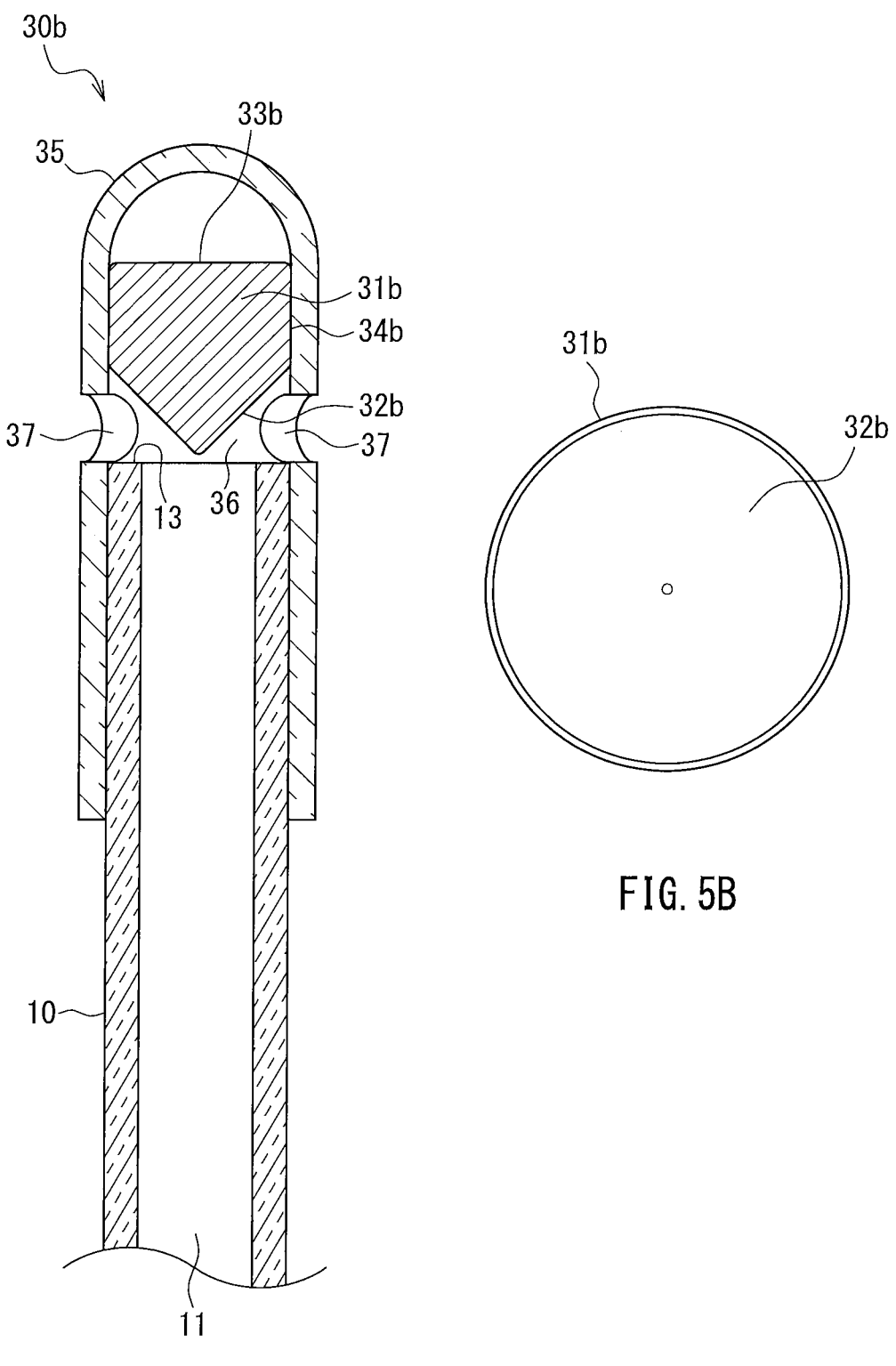
FIG. 5A is a cross-sectional view of yet another light emitting portion according to Embodiment 1 of the present invention.
FIG. 5B is a front view of a reflective surface of a reflective member of the light emitting portion.

Alternatively, as shown in FIGS. 5A and 5B, a light emitting portion 30b may include a reflective member 31b that has a conical surface 32b as a reflective surface. The conical surface 32b is arranged coaxially with the tube 10 such that it is spaced apart from the end surface 13 and opposes the end surface 13. Light emerging from the end surface 13 is reflected by the conical surface 32b and passes through the housing 35. The reflective member 31b includes a flat surface 33b that is located on a side opposite to the conical surface 32b and a cylindrical surface 34b that connects the conical surface 32b and the flat surface 33b. This reflective member 31b can be produced with ease by cutting (e.g., lathe cutting) a metal material.

The reflective member may also have any convex curved surface other than the spherical surface 32 and the concave pyramidal or conical surfaces 32a and 32b as the reflective surface on the side opposing the end surface 13. The reflective surface of the reflective member does not need to be a convex surface, and may also be a concave surface. The entire reflective member does not need to have a solid shape, and may have, for example, a ring shape that opposes the end surface 13. A ring-shaped reflective member may be spaced apart from the end surface 13 or may be in contact with the end surface 13 (see FIG. 6A, which will be described later). A configuration may also be adopted in which the nutrient flowing out of the distal end of the tube 10 flows through the central opening of the ring-shaped reflective member.

The housing 35 itself may also have the function of a reflective member. For example, the housing 35 is provided with, as a reflective surface, a surface that opposes the end surface 13. Light emerging from the end surface 13 is reflected by this reflective surface of the housing 35. The reflective surface may have any shape, such as a spherical surface shape, a pyramidal/conical surface shape, or a ring shape. The reflective surface is not limited to a convex surface, and may also be a concave surface. The reflective member may be spaced apart from the end surface 13 or may be in contact with the end surface 13. In the case where the housing 35 has a reflective surface, the light emitting portion is no longer required to have a reflective surface separately from the housing 35. Thus, the configuration of the light emitting portion is simplified. Note that a portion of light incident on the reflective surface of the housing 35 may enter the reflective surface and emerge from an outer surface of the housing 35. The light may be refracted when entering the housing 35 and when emerging from the housing 35. That is to say, the housing 35 may also function as a refractive member (see Embodiment 2, which will be described later) in addition to a reflective member. The reflective surface of the housing 35 may be provided with a metal vapor deposition layer or any of various types of coating layers.

Figure 6C:
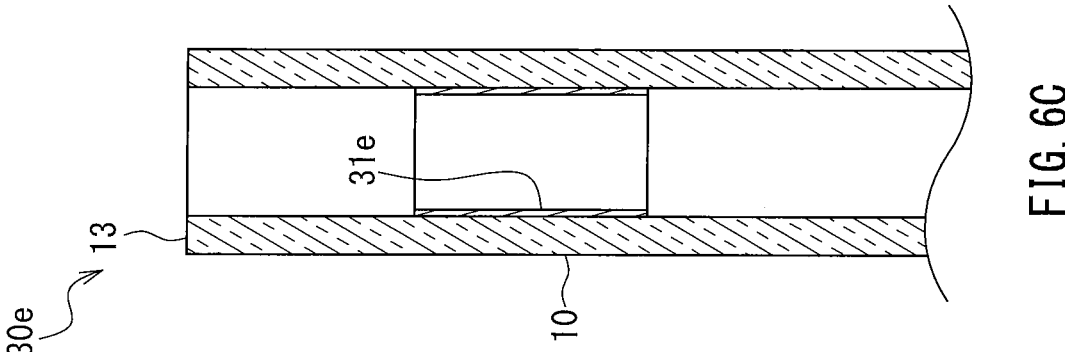
FIGS. 6A to 6C are cross-sectional views of other light emitting portions according to Embodiment 1 of the present invention.
Figure 6B:
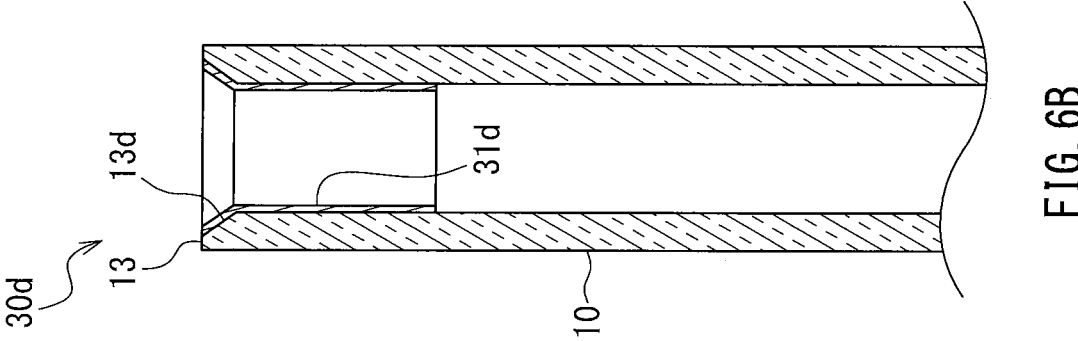
Figure 6A:
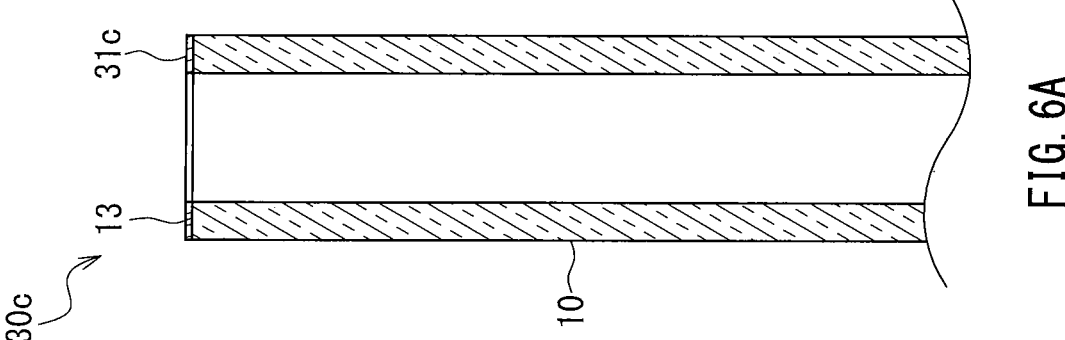

A reflective member may be provided in direct contact with the tube 10. In the present invention, such a reflective member is referred to as a "direct contact-type reflective member". For example, as shown in FIG. 6A, a light emitting portion 30c may include a direct contact-type reflective member 31c provided on the end surface 13 of the tube 10. Alternatively, as shown in FIG. 6B, a light emitting portion 30d may include a direct contact-type reflective member 31d provided in a region near the end surface 13, of the inner surface of the tube 10. Alternatively, as shown in FIG. 6C, a light emitting portion 30e may include a direct contact-type reflective member 31e provided in a region slightly apart from the end surface 13, of the inner surface of the tube 10. Although there is no limitation on the direct contact-type reflective member, examples thereof include a metal vapor deposition layer and various types of coating layers, and a metal vapor deposition layer is particularly preferable. Alternatively, a reflective member prepared as a member that is separate from the tube 10 may be fixed to the tube 10 and used as a direct contact-type reflective member. Light from the thickness portion of the tube 10 is incident on the direct contact-type reflective member, is reflected by this reflective member, passes through the thickness portion of the tube 10 again, and emerges from the tube 10 (e.g., from the outer surface of the tube 10). A light emitting portion including a direct contact-type reflective member has a simple configuration and is easily provided in the tube. Also, the light emitting portion no longer needs to have the housing 35. If the housing 35 is omitted, there is no light loss due to light passing through the housing 35. Furthermore, it is unlikely that light loss will occur due to the presence of the nutrient between the tube 10 and the reflective member. The direct contact-type reflective member may also be provided on the outer surface of the tube 10.

In general, it is difficult to control the orientation of the light emitting portion in the patient's body, and it is therefore preferable that light is emitted from the light emitting portion in various directions, including the radial direction. For this purpose, it is desired that the light emitting portion emits more light substantially along the radial direction of the tube 10 rather than the longitudinal direction of the tube 10. In FIG. 6B, a conical chamfer 13d is formed at an opening edge that defines the opening at the end surface 13 of the tube 10, and the reflective member 31d is also provided on the chamfer 13d. In this manner, light incident on the chamfer 13d can be reflected radially outward. Thus, a relatively small amount of light is emitted from the end surface 13 substantially along the longitudinal direction of the tube 10. In FIG. 6C, the reflective member 31e is provided spaced apart from the end surface 13. Most of light is reflected by the reflective member 31e and emerges from the tube 10 substantially along the radial direction. Thus, a small amount of light reaches the end surface 13. As a result, a relatively small amount of light emerges from the end surface 13 substantially along the longitudinal direction of the tube 10.

In order to increase the amount of light emerging from the tube 10, the coating material with a low refractive index, the metal vapor deposition layer, the low refractive index material layer, or the like (hereinafter, these will be collectively referred to as a "leaked light prevention layer"), which is provided on the tube 10 to reduce leaked light, may be removed from a region where light emerges. Additionally or alternatively, minute protrusions and depressions may be provided in a region of the outer surface of the tube 10 where light emerges. The "minute protrusions and depressions" may be irregular protrusions and depressions such as those of a satin finished surface or may be regular protrusions and depressions such as those of a knurled surface or a bellows shape. The minute protrusions and depressions also have a diffusing effect that causes light to emerge from the tube 10 in various directions.

Embodiment 2

Figures 7A, 7B:
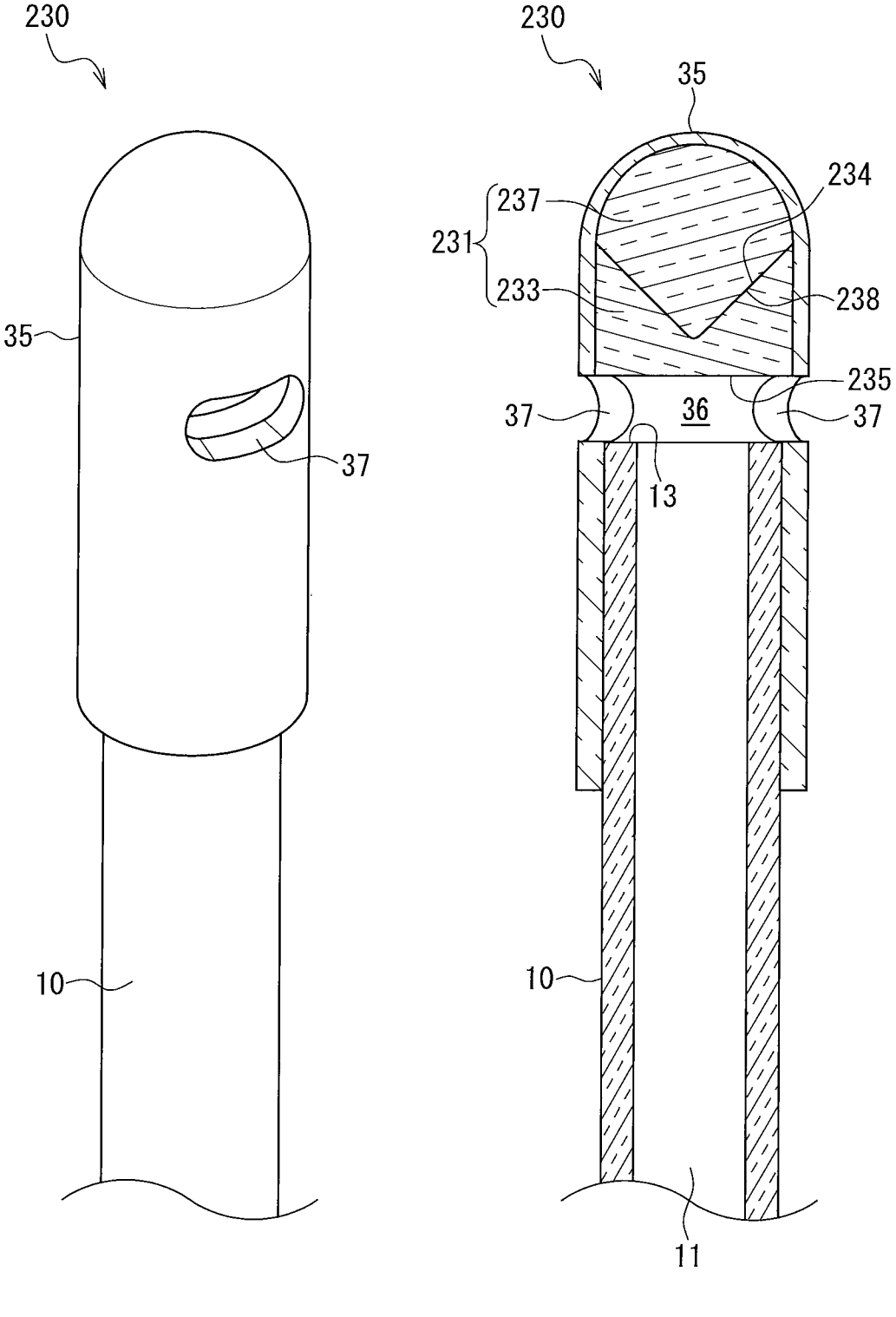
FIG. 7A is a perspective view of a light emitting portion according to Embodiment 2 of the present invention.
FIG. 7B is a cross-sectional view of the light emitting portion.

Embodiment 2 is different from Embodiment 1 in terms of the light emitting portion. FIG. 7A is a perspective view of a light emitting portion 230 according to Embodiment 2. FIG. 7B is a cross-sectional view of the light emitting portion 230. As shown in FIG. 7B, the light emitting portion 230 of Embodiment 2 includes a refractive member 231 instead of the reflective member 31 (see FIG. 3B) of Embodiment 1. The refractive member 231 is formed by combining a first prism 233 and a second prism 237 that have different refractive indices.

FIG. 8A is an exploded perspective view of the light emitting portion 230 as viewed from the distal end side, and FIG. 8B is an exploded perspective view of the light emitting portion 230 as viewed from the base end side. In FIGS. 8A and 8B, the housing 35 (see FIGS. 7A and 7B) is not shown. The first prism 233 includes a concave pyramidal surface 234 that opposes the second prism 237, a flat surface 235 that opposes the tube 10, and a cylindrical surface 236 that connects an outer circumferential edge of the concave pyramidal surface 234 and an outer circumferential edge of the flat surface 235. The second prism 237 includes a convex pyramidal surface 238 that opposes the first prism 233 and a convex curved surface (spherical surface) 239 located on a side opposite to the first prism 233. The concave pyramidal surface 234 has a shape obtained by cutting a square pyramidal surface at the cylindrical surface 236 that is coaxial with the square pyramidal surface. The convex pyramidal surface 238 has the same geometrical shape as the concave pyramidal surface 234. As shown in FIG. 7B, the first prism 233 and the second prism 237 are joined and combined together so that four side faces of the concave pyramidal surface 234 are in surface contact with four respective side faces of the convex pyramidal surface 238. The flat surface 235 of the first prism 233 is parallel to and spaced apart from the end surface 13 of the tube 10. The cylindrical surface 236 of the first prism 233 and the convex curved surface 239 of the second prism 237 are in areal contact with the inner surface of the housing 35. The first and second prisms 233 and 237 are arranged coaxially with the tube 10. Although there is no limitation on the outer diameters of the first and second prisms 233 and 237, it is preferable that the outer diameters are equal to or slightly larger than the outer diameter of the tube 10.

The first prism 233 and the second prism 237 are made of hard and translucent or transparent materials. Although there is no limitation on the materials of the first and second prisms 233 and 237, materials that are commonly used as optical materials are preferable, or more specifically, glass and resin materials, such as a polymethyl methacrylate resin (PMMA), polystyrene, polycarbonate, and polyolefin, are preferable. The first prism 233 and the second prism 237 are made of materials having different refractive indices.

Light that has passed through the tube 10 and emerged from the end surface 13 is incident on the flat surface 235, and a portion of the light passes through a joint surface between the concave pyramidal surface 234 and the convex pyramidal surface 238, the convex curved surface 239, and the housing 35 in that order, while another portion of the light passes through the cylindrical surface 236 and the housing 35 in that order. Light is refracted when passing through a boundary surface (refractive surface) where the refractive index changes, such as the flat surface 235, the joint surface between the concave pyramidal surface 234 and the convex pyramidal surface 238, the convex curved surface 239, and the cylindrical surface 236. The refractive member 231 refracts light from the end surface 13 in various directions, and therefore, as with the reflective member 31 of Embodiment 1, light from the light emitting portion 230 can be observed on the body surface of the patient 90 irrespective of the orientation of the light emitting portion 230.

In the above-described embodiment, the shape of the joint surface (the concave pyramidal surface 234 and the convex pyramidal surface 238) between the first prism 233 and the second prism 237 constitutes a portion of the square pyramidal surface. However, the present invention is not limited to this. The shape of the joint surface between the first prism 233 and the second prism 237 may constitute a portion of any regular polygonal surface or may constitute a conical surface. The shape of the joint surface between the first prism 233 and the second prism 237 is not limited to a pyramidal or conical shape, and may be a spherical surface or any desired curved surface. A configuration may also be adopted in which the first prism 233 has a convex surface, and the second prism 237 has a concave surface to be joined to the convex surface.

Light incident on the above-described refractive surface may be partially or entirely reflected by the joint surface.

The refractive member may be constituted by three or more prisms.

The refractive member may be constituted by a single prism. For example, the refractive member may be constituted by only the second prism 237. In this case, light emerging from the end surface 13 is refracted when passing through the convex pyramidal surface 238 and the convex curved surface 239.

The second prism 237 may be formed integrally with the housing 35 using the same material as the housing 35. In this case, the first prism 233 may be present or may be omitted.

FIG. 9A is a cross-sectional view of another light emitting portion 230a according to Embodiment 2. The light emitting portion 230a includes a refractive member 231a consisting of a single prism. FIG. 9B is an exploded perspective view of the light emitting portion 230a as viewed from the distal end side. In FIG. 9B, the housing 35 (see FIG. 9A) is not shown. The refractive member (prism) 231a has a flat surface 235a that opposes the tube 10, a convex pyramidal surface 234a that is located on a side opposite to the flat surface 235a, and a cylindrical surface 236a that connects an outer circumferential edge of the flat surface 235a and an outer circumferential edge of the convex pyramidal surface 234a. The convex pyramidal surface 234a has a shape obtained by cutting a square pyramidal surface at the cylindrical surface 236a that is coaxial with the square pyramidal surface. As shown in FIG. 9A, the flat surface 235a is parallel to and spaced apart from the end surface 13 of the tube 10. The cylindrical surface 236a is in areal contact with the inner surface of the housing 35. The refractive member 231a is arranged coaxially with the tube 10. Light emerging from the end surface 13 is incident on the flat surface 235a, and a portion of the light passes through the convex pyramidal surface 234a and the housing 35 in that order, while another portion of the light passes through the cylindrical surface 236a and the housing 35 in that order. Light is refracted when passing through a boundary surface (refractive surface) where the refractive index changes, such as the flat surface 235a, the convex pyramidal surface 234a, and the cylindrical surface 236a. The convex pyramidal surface 234a may be any pyramidal surface or conical surface.

Figure 10:
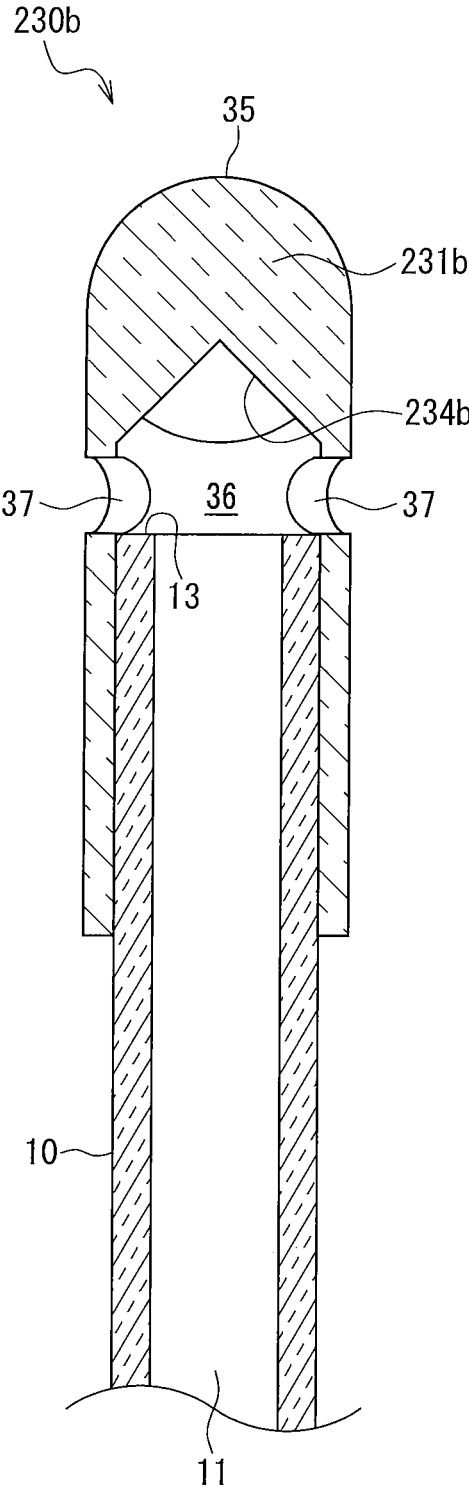
FIG. 10 is a cross-sectional view of yet another light emitting portion according to Embodiment 2 of the present invention.

FIG. 10 is a cross-sectional view of yet another light emitting portion 230b according to Embodiment 2. In the light emitting portion 230b shown in FIG. 10, a refractive member (prism) 231b made of the same material as the housing 35 is formed integrally with the housing 35. That is to say, a concave pyramidal surface 234b is provided at the inner surface of the housing 35. The concave pyramidal surface 234b has a shape obtained by cutting a square pyramidal surface at the cylindrical surface (inner circumferential surface of the housing 35) that is coaxial with the square pyramidal surface. The concave pyramidal surface 234b is arranged coaxially with the tube 10 such that it is spaced apart from the end surface 13 and opposes the end surface 13. Light emerging from the end surface 13 is refracted when entering the concave pyramidal surface 234b, passes through the refractive member 231b, and emerges from the outer surface of the housing 35. The concave pyramidal surface 234b may be any pyramidal surface or conical surface.

The refractive surface of a refractive member may have any shape such as a convex surface (convex curved surface or convex pyramidal or conical surface), a concave surface (concave curved surface or concave pyramidal or conical surface), a flat surface, or the like. Minute protrusions and depressions described in Embodiment 1 may also be provided on the refractive surface.

Embodiment 2 is the same as Embodiment 1 except for the above-described differences. The description of Embodiment 1 is also applicable to Embodiment 2.

Embodiment 3

Embodiment 3 is different from Embodiments 1 and 2 in terms of the light emitting portion. A light emitting portion of Embodiment 3 includes a distal end of a tube 10 that is formed so as to allow light to be refracted when emerging from the tube 10 and therefore emerge in various directions.

Figures 11A, 11B:
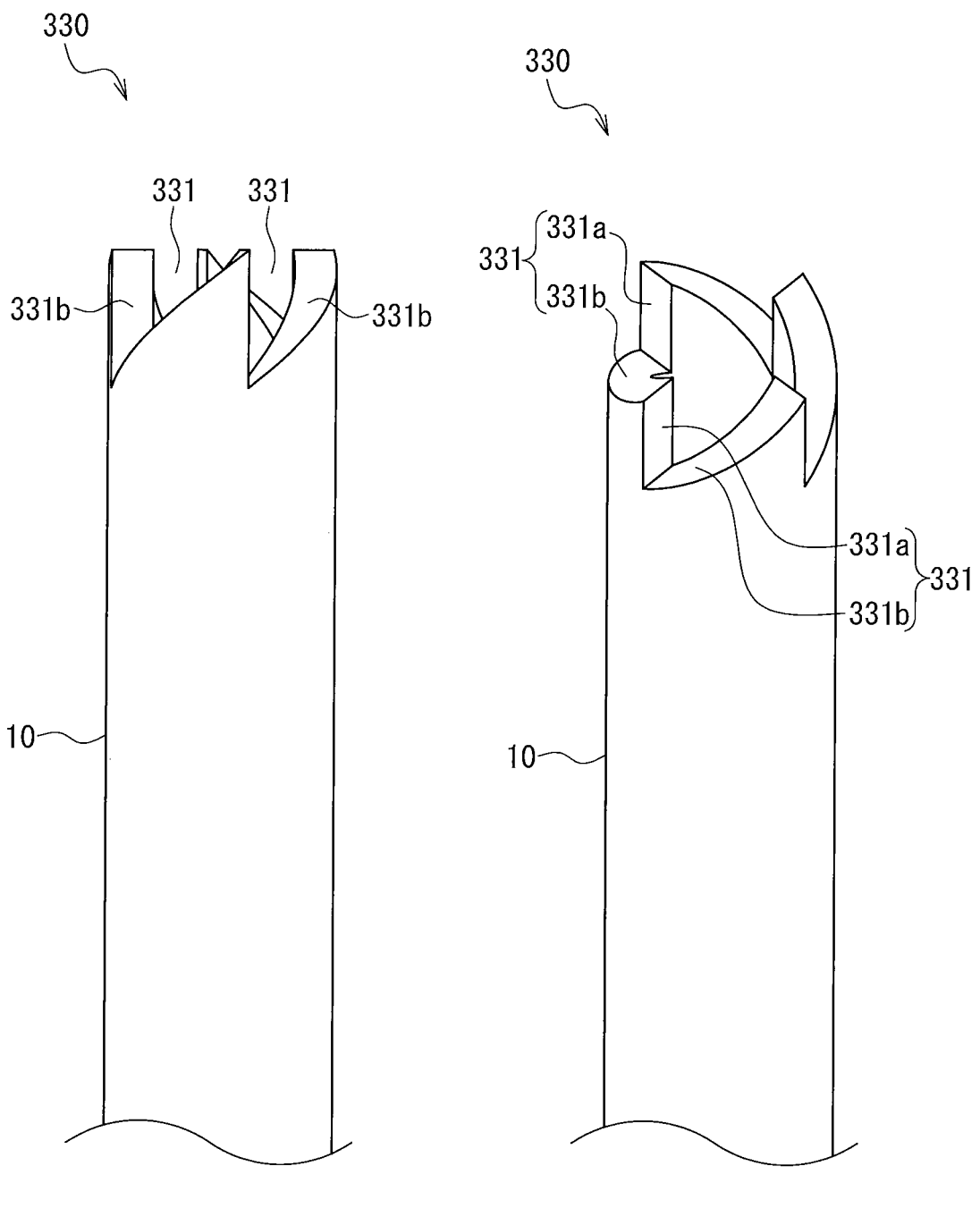
FIG. 11A is a side view of a light emitting portion according to Embodiment 3 of the present invention.
FIG. 11B is a perspective view of the light emitting portion.

FIG. 11A is a side view of a light emitting portion 330 according to Embodiment 3, and FIG. 11B is a perspective view of the light emitting portion 330. The light emitting portion 330 includes none of the reflective members 31 and 31a to 31e of Embodiment 1 and the refractive members 231, 231a, and 231b of Embodiment 2. The light emitting portion 330 has four wedge-shaped notches 331 formed at the distal end of the tube 10. The four notches 331 are arranged adjacent to each other at regular intervals in the circumferential direction of the tube 10. Each notch 331 is constituted by a first surface 331a that is parallel to the longitudinal direction of the tube 10 and a second surface 331b that is inclined with respect to the first surface 331a. The first surface 331a and the second surface 331b are connected to each other at the deepest portion of the notch 331.

Light that has passed through the tube 10 is refracted when emerging from the first surface 331a and the second surface 331b. Since the first and second surfaces 331a and 331b are arranged at regular angular intervals in the circumferential direction of the tube 10, light emerging from first and second surfaces 331a and 331b travels in various directions. As in the case of Embodiments 1 and 2, light from the light emitting portion 330 can be observed on the body surface of the patient 90 irrespective of the orientation of the light emitting portion 330.

The light emitting portion 330 may have a housing that is similar to the housing 35 of Embodiments 1 and 2. In this case, the distal end of the tube 10 where the notches 331 are formed is housed in the housing. The housing may also incorporate a weight for facilitating the insertion of the tube 10 into the digestive tract. In this case, the weight is spaced apart from the notches 331 in the longitudinal direction of the tube 10.

The shape of the notches 331 is not limited to a substantially right triangle such as that described above, and may be any triangle such as an isosceles triangle. Alternatively, the shape of the notches 331 may be any polygon (e.g., a trapezoid) other than a triangle, or may be any curve. Also, the number of notches 331 is not limited to the number in the above-described embodiment. The notches 331 do not have to be arranged at regular intervals in the circumferential direction.

In the above-described embodiment, the light emitting portion 330 has a plurality of notches 331; however, the present invention is not limited to this configuration. It is sufficient that a shape for refracting light so that light that has passed through the tube 10 emerges obliquely with respect to the longitudinal direction of the tube 10 is provided at the distal end of the tube 10. For example, the end surface at the distal end of the tube 10 may be a conical surface whose inner diameter gradually increases toward the distal end or a conical surface whose outer diameter gradually decreases toward the distal end. In these cases as well, light can be refracted in various directions when emerging.

FIG. 12A is a perspective view of another light emitting portion 330a according to Embodiment 3. FIG. 12B is a cross-sectional view of the light emitting portion 330a. A distal end portion of the tube 10 is divided into a plurality of branch portions 332 by a plurality of slits formed along the longitudinal direction of the tube 10. The plurality of branch portions 332 are curved radially outward so as to form a flared shape. The branch portions 332 adjacent to each other in the circumferential direction are spaced apart from each other. Light that has passed through the tube 10 emerges from side surfaces and distal end surfaces of the branch portions 332. Light is refracted when emerging from the various surfaces of the branch portions 332. Since the plurality of branch portions 332 are curved in different directions, light emerging from the various surfaces of the branch portions 332 travels in various directions. Light from the light emitting portion 330*a* can be observed on the body surface of the patient 90 irrespective of the orientation of the light emitting portion 330*a*. In the distal end portion of the tube 10, where the plurality of branch portions 332 are formed, the leaked light prevention layer provided on the tube 10 may be removed.

Figures 13A, 13B:
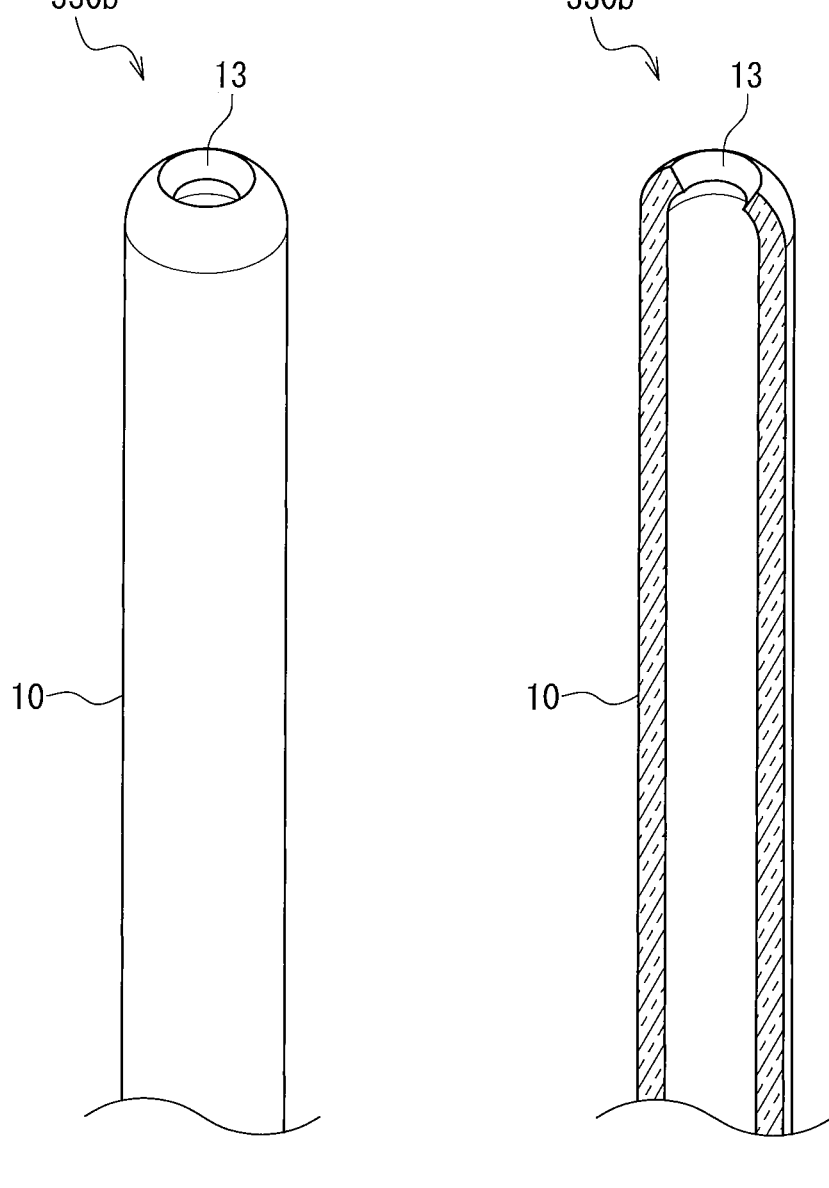
FIG. 13A is a perspective view of yet another light emitting portion according to Embodiment 3 of the present invention.
FIG. 13B is a cross-sectional perspective view of the light emitting portion.

FIG. 13A is a perspective view of yet another light emitting portion 330*b* according to Embodiment 3. FIG. 13B is a cross-sectional perspective view of the light emitting portion 330*b*. A distal end portion of a tube 10 is curved radially inward. An end surface 13 at the distal end of the tube 10 forms a substantially concave conical surface. Light that has passed through the tube 10 emerges from the end surface 13. Light is refracted when emerging from the end surface 13. Since the end surface 13 is curved into a substantially concave conical surface shape, light emerging from the end surface 13 is temporarily converged and then diverged like light emerging from a convex lens. Thus, light from the light emitting portion 330*b* can be observed on the body surface of the patient 90 irrespective of the orientation of the light emitting portion 330*b*.

FIG. 14A is a perspective view of yet another light emitting portion 330*c* according to Embodiment 3. FIG. 14B is a cross-sectional perspective view of the light emitting portion 330*c*. A plurality of slot-like holes 333 extending through the tube 10 in the radial direction are formed near the distal end of the tube 10. Most of light passing through the tube 10 emerges from side surfaces (surfaces that define the holes 333 and that connect the inner surface and the outer surface of the tube 10) of the holes 333 before reaching the end surface 13. Light is refracted when emerging from the side surfaces. The plurality of holes 333 are arranged at substantially regular intervals in the circumferential direction, and therefore, light emerging from the side surfaces of the holes 333 travels in various directions. Thus, a relatively small amount of light emerges from the end surface 13 substantially along the longitudinal direction of the tube 10. Light from the light emitting portion 330*c* can be observed on the body surface of the patient 90 irrespective of the orientation of the light emitting portion 330*c*. Although the longitudinal direction of the holes 333 may be parallel to the longitudinal direction of the tube 10, it is preferable that, as shown in FIGS. 14A and 14B, the longitudinal direction of the holes 333 is slightly inclined with respect to the longitudinal direction of the tube 10. This is advantageous for widely diffusing light when it emerges from the light emitting portion 330*c*. The number of holes 333 may be set to any number.

Figures 15A, 15B:
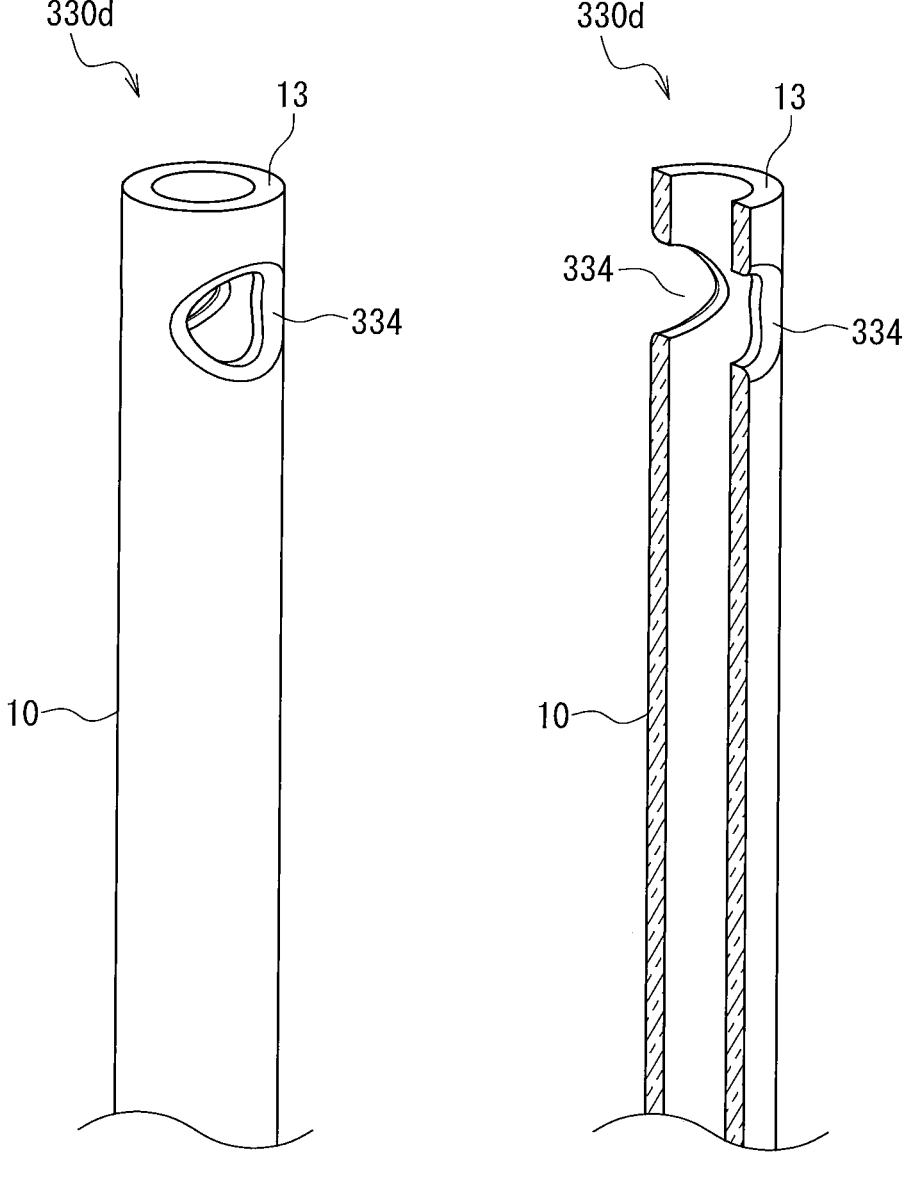
FIG. 15A is a perspective view of yet another light emitting portion according to Embodiment 3 of the present invention.
FIG. 15B is a cross-sectional perspective view of the light emitting portion.

FIG. 15A is a perspective view of yet another light emitting portion 330*d* according to Embodiment 3. FIG. 15B is a cross-sectional perspective view of the light emitting portion 330*d*. One or more (two in the present example) substantially elliptical (or substantially circular) holes 334 extending through the tube 10 in the radial direction are formed near the distal end of the tube 10. A portion of light passing through the tube 10 emerges from a side surface (surface that defines each hole 334 and that connects the inner surface and the outer surface of the tube 10) of each hole 334 before reaching the end surface 13. Light is refracted when emerging from the side surface. The plurality of holes 334 are arranged discretely in the circumferential direction, and the side surface of each hole 334 constitutes a substantially elliptical (or substantially circular) closed surface. Therefore, light emerging from the side surfaces of the holes 334 travels in various directions. Thus, a relatively small amount of light emerges from the end surface 13 substantially along the longitudinal direction of the tube 10. Light from the light emitting portion 330*d* can be observed on the body surface of the patient 90 irrespective of the orientation of the light emitting portion 330*d*. The number of holes 334 may be set to any number, but a greater number is preferred, and specifically it is preferable that the number of holes 334 is four or more. The greater the number of holes 334, the more widely light can be diffused when it emerges from the light emitting portion 330*d*.

In the light emitting portion 330*c* or 330*d*, the holes 333 or 334 may have any shape, and examples include an ellipse, a circle, various polygons (a triangle, a quadrangle, a pentagon, etc.), a circular arc shape, a "V" shape, and the like. The number of holes 333 or 334 may be set to any number; there need not be more than one hole 333 or 334, and the number of holes may be one. Also, the holes 333 or 334 may be arranged in any pattern. In the case where a plurality of holes 333 or 334 are formed, the holes may or may not be arranged at substantially regular intervals in the circumferential direction. A plurality of rows of holes 333 or 334 arranged in the circumferential direction of the tube 10 may be formed at a plurality of positions, respectively, in the longitudinal direction of the tube 10.

The light emitting portion 330*c* or 330*d* may have a recess that does not extend through the tube 10, instead of the holes 333 or 334 that extend through the tube 10. The recess may be formed on either the inner surface or the outer surface of the tube 10. Light is refracted when emerging from a surface that defines the recess.

A high refractive index layer (layer having a higher refractive index than the material of the tube 10), or minute protrusions and depressions described in Embodiment 1, may be provided on the end surface 13 at the distal end of the tube 10 and/or a region of the inner surface and/or the outer surface of the tube 10 that is located near the distal end. Alternatively, the leaked light prevention layer may be removed from a region of the inner surface and/or the outer surface of the tube 10 that is located near the distal end. Two or more of the provision of the high refractive index layer, the provision of the minute protrusions and depressions, and the removal of the leaked light prevention layer may also be used in combination. Light emerges from a region (light emitting region) that has been subjected to such processing while being refracted. The light emitting region may be provided at any position. As with the position where the direct contact-type reflective member described in Embodiment 1 is provided, providing the light emitting region at a position slightly spaced apart from the end surface 13 of the tube 10 allows less light to reach the end surface 13 of the tube 10 and is therefore advantageous for causing light to emerge in various directions.

The light emitting portions 330*a* to 330*d* may have a housing that is similar to the housing 35 of Embodiments 1 and 2. In this case, the distal end portion of the tube 10 that is configured so that light emerges while being refracted is housed in the housing. The housing may also incorporate a weight for facilitating the insertion of the tube 10 into the digestive tract. In this case, the weight is spaced apart from the distal end of the tube 10 in the longitudinal direction of the tube 10.

As described above, the light emitting portion according to Embodiment 3 includes a structure for causing light to emerge in various directions, including the radial direction, the structure being provided in the tube itself. The light emitting portion of Embodiment 3 does not need to include the reflective member of Embodiment 1 or the refractive member of Embodiment 2. For this reason, the light emitting portion is constituted by a small number of members, and has a simple configuration. Moreover, light loss that can be caused by the tube and the reflective member or the refractive member being spaced apart from each other does not occur in Embodiment 3. However, the light emitting portion of Embodiment 3 may be combined with the reflective member of Embodiment 1 or the refractive member of Embodiment 2.

Embodiment 3 is the same as Embodiment 1 except for the above-described differences. The description of Embodiment 1 is also applicable to Embodiment 3.

It should be understood that Embodiments 1 to 3 above are given by way of example only. The present invention is not limited to Embodiments 1 to 3 above, and modifications can be made thereto as appropriate.

Although the present invention has been applied to oral or nasal tube feeding in Embodiments 1 to 3 above, the present invention can also be applied to any other field in which a tube is inserted into the human body. For example, the present invention can be applied to a case in which a catheter (tube) is inserted into an artery or a vein. The liquid flowing through the tube can be any liquid, such as a nutrient, a drug, a contrast medium, or blood. The configurations of the connector, the light emitting portion, the tube, and the like can be changed according to the field of application.

The connector provided at the base end of the tube is not limited to the male connector 20 described in Embodiments 1 to 3. The connector does not need to include the female thread 24, and even does not need to include the outer cylinder 23. The shape of the male member 21 can be changed as desired. The connector may also be a female connector.

INDUSTRIAL APPLICABILITY

The present invention can be widely used in the field of medicine. For example, the present invention can be suitably used for tube feeding, and particularly for oral or nasal tube feeding.

LIST OF REFERENCE NUMERALS

1 Medical tube distal end position detection system
10 Tube
11 Flow path
12 End surface at base end of tube
13 End surface at distal end of tube
20 Connector
21 Male member
23 Outer cylinder
24 Female thread
30, 30*a* to 30*e*, 230, 230*a* to 230*b*, 330, 330*a* to 330*d* Light emitting portion
31, 31*a* to 31*e* Reflective member
32 Spherical surface
32*a*, 32*b* Pyramidal or conical surface
35 Housing
37 Hole in housing
231, 231*a*, 231*b* Refractive member
333, 334 Hole extending through tube
50 Light source device

20

The invention claimed is:

1. A medical tube distal end position detection system for detecting a position of a distal end of a tube inserted into a patient, the system comprising:
a light source device that emits light;
a hollow tube having a flow path that allows a liquid to flow therethrough;
a connector provided at a base end of the tube so as to allow the light from the light source device to be incident on an end surface at the base end of the tube; and
a light emitting portion provided at the distal end of the tube,
wherein the tube comprises a three-layer structure of an inner layer, an outer layer, and an intermediate layer provided between the inner layer and the outer layer, in which the intermediate layer has a higher refractive index than the inner layer and the outer layer, and the inner layer, the outer layer, and the intermediate layer are each made of resin,
the system is configured so that the light from the light source device is allowed to pass through the intermediate layer of the tube and be emitted from the light emitting portion, and the light from the light emitting portion is allowed to be transmitted to a body surface,
wherein the light emitting portion includes a refractive member that refracts light emerging from the tube,
the refractive member is arranged coaxially with the tube, and
an outer diameter of the refractive member is larger than an outer diameter of the tube.

2. The medical tube distal end position detection system according to claim 1,
wherein the light emitted by the light source device has a wavelength of 360 nm to 3,000 nm.

3. The medical tube distal end position detection system according to claim 1, wherein the connector has a cylindrical male member into which the tube is inserted, an outer cylinder surrounding the cylindrical male member, and a female thread formed on an inner circumferential surface of the outer cylinder that opposes the cylindrical male member.

4. The medical tube distal end position detection system according to claim 3, wherein the end surface at the base end of the tube is exposed at an opening at a leading end of the cylindrical male member.

5. The medical tube distal end position detection system according to claim 1, wherein the light emitting portion comprises a reflective member that reflects the light emerging from the tube.

6. The medical tube distal end position detection system according to claim 5, wherein the reflective member has a spherical surface or a pyramidal or conical surface on a side thereof that opposes an end surface at the distal end of the tube.

7. The medical tube distal end position detection system according to claim 5, wherein the reflective member is made of titanium.

8. The medical tube distal end position detection system according to claim 5, wherein the reflective member is provided in direct contact with the tube.

9. The medical tube distal end position detection system according to claim 8, wherein the reflective member is a metal vapor deposition layer.

10. The medical tube distal end position detection system according to claim 1, wherein the light emitting portion comprises a refractive member that refracts the light emerging from the tube.

11. The medical tube distal end position detection system according to claim 1, wherein the light emitting portion comprises the distal end of the tube that is formed so that the light that has passed through the tube emerges therefrom while being refracted.

12. The medical tube distal end position detection system according to claim 1, wherein the light emitting portion comprises a hole extending through the tube or a recess formed on the inner surface or the outer surface of the tube.

13. The medical tube distal end position detection system according to claim 1, wherein a leaked light prevention layer for preventing the light in a process of passing through the tube from emerging from the outer surface of the tube, is provided on the outer surface of the tube, and the leaked light prevention layer is removed from the light emitting portion.

14. The medical tube distal end position detection system according to claim 1, wherein the light emitting portion has a housing, and the housing has a hole that allows the liquid that has flowed through the tube to flow out to an outside.

15. The medical tube distal end position detection system according to claim 1, wherein the light emitting portion has a translucent or transparent housing.

16. The medical tube distal end position detection system according to claim 1, wherein the outer surface of the tube has a surface roughness Ra of 1.2 μm or less.

17. The medical tube distal end position detection system according to claim 1, wherein the outer surface of the tube is covered by a coating material having a refractive index that is lower than a refractive index of the tube.

18. The medical tube distal end position detection system according to claim 1, further comprising a stylet or an optical fiber that can be removably inserted into the flow path of the tube.

19. The medical tube distal end position detection system according to claim 1, wherein the outer layer contains fluorine.

\* \* \* \* \*